United States Patent
Wernke et al.

(10) Patent No.: US 11,464,438 B2
(45) Date of Patent: Oct. 11, 2022

(54) CONDUCTIVE HUMAN INTERFACES

(71) Applicant: WillowWood Global LLC, Mt. Sterling, OH (US)

(72) Inventors: Matthew Wernke, Columbus, OH (US); Ryan Schroeder, Westerville, OH (US); James M. Colvin, Hilliard, OH (US); Michael L. Haynes, Columbus, OH (US); Stephen A. Byers, Dublin, OH (US); Christopher T. Kelley, Grandview Heights, OH (US); Anne Marie Jackson, Grove City, OH (US)

(73) Assignee: WILLOWWOOD GLOBAL LLC, Mt. Sterling, OH (US)

( * ) Notice: Subject to any disclaimer, the term of this patent is extended or adjusted under 35 U.S.C. 154(b) by 1382 days.

(21) Appl. No.: 15/675,088

(22) Filed: Aug. 11, 2017

(65) Prior Publication Data
US 2018/0042509 A1 Feb. 15, 2018

Related U.S. Application Data

(60) Provisional application No. 62/373,670, filed on Aug. 11, 2016.

(51) Int. Cl.
*A61F 2/48* (2006.01)
*A61B 5/05* (2021.01)
(Continued)

(52) U.S. Cl.
CPC ............ *A61B 5/296* (2021.01); *A61B 5/6811* (2013.01); *A61B 5/6824* (2013.01);
(Continued)

(58) Field of Classification Search
CPC ........ A61F 2/72; A61F 2/68; A61F 2002/704; A61F 2/583; A61F 2/54;
(Continued)

(56) References Cited

U.S. PATENT DOCUMENTS

| | | | |
|---|---|---|---|
| 4,522,211 A | * | 6/1985 | Bare ...................... A61B 5/259 600/392 |
| 4,898,783 A | | 2/1990 | McCullough, Jr. et al. |

(Continued)

FOREIGN PATENT DOCUMENTS

| | | |
|---|---|---|
| DE | 102014106070 A1 | 11/2015 |
| WO | 00/71024 A1 | 11/2000 |

(Continued)

OTHER PUBLICATIONS

Thomas, S., "From Snap Fits to Adhesives: A Comprehensive Guide to Mechanical Fastener Options," 21 pages (May 2016).
(Continued)

*Primary Examiner* — Joseph A Stoklosa
*Assistant Examiner* — Brian M Antiskay
(74) *Attorney, Agent, or Firm* — Thompson Hine LLP

(57) ABSTRACT

A conductive human interface has a fabric layer with an interior surface and an exterior surface. A soft coating overlies the interior surface of the fabric layer. An electrode or sensor is included to connect with a residual limb. A conductive path connects the electrode or sensor with an electrical connector which, in turn connects with a prosthetic or other assistive device. The conductive path includes a conductor having a section overlying the fabric layer. The overlying section of the conductor can be cord of conductive thread. A nonconductive support thread can extend through the fabric layer from the exterior surface to the interior surface, and further around the conductor to secure the overlying section of the conductor to the fabric layer.

19 Claims, 17 Drawing Sheets

(51) Int. Cl.
*A61B 5/296* (2021.01)
*A61B 5/00* (2006.01)
*D01F 1/09* (2006.01)
*A61B 5/389* (2021.01)

(52) U.S. Cl.
CPC .......... *A61B 5/6825* (2013.01); *A61B 5/6828* (2013.01); *A61B 5/6831* (2013.01); *A61B 5/389* (2021.01); *A61B 2562/125* (2013.01); *A61B 2562/222* (2013.01); *A61B 2562/227* (2013.01); *D01F 1/09* (2013.01); *D10B 2401/16* (2013.01); *D10B 2401/18* (2013.01)

(58) Field of Classification Search
CPC .. A61F 2002/7615; A61F 2/60; A61F 2/7812; A61F 2/70; A61F 2/76; A61B 5/04001; A61B 5/0478; A61B 5/0484; A61B 5/0488; A61B 5/7264; A61B 5/04012; A61B 5/0482; A61B 5/04888; A61B 5/4851; A61B 5/04085
USPC ................ 600/372, 382, 386, 388–390, 393, 600/544–545; 607/115; 623/24–25, 33, 623/36–37, 58–65
See application file for complete search history.

(56) References Cited

U.S. PATENT DOCUMENTS

| | | | |
|---|---|---|---|
| 5,443,525 A | | 8/1995 | Laghi |
| 5,606,149 A | | 2/1997 | Yaworski et al. |
| 6,803,332 B2* | 10/2004 | Andrews ................ D02G 3/12 428/377 |
| 8,123,568 B2* | 2/2012 | Meyer ................ H01R 4/4845 439/668 |
| 8,320,988 B2* | 11/2012 | Axelgaard ........... A61N 1/0452 600/391 |
| 8,591,599 B1 | 11/2013 | Kaliki et al. |
| 8,948,839 B1* | 2/2015 | Longinotti-Buitoni ..................... A61B 5/6805 600/382 |
| 8,971,983 B2* | 3/2015 | Gilmore ................ A61B 5/296 600/391 |
| 8,979,944 B2 | 3/2015 | Laghi et al. |
| 9,155,634 B2 | 10/2015 | Lipschutz et al. |
| 9,293,901 B2* | 3/2016 | Lind ....................... H02G 3/32 |
| 2003/0175513 A1 | 9/2003 | Tokarsky et al. |
| 2004/0015222 A1 | 1/2004 | Nielsen |
| 2005/0049481 A1 | 3/2005 | Gray et al. |
| 2005/0184619 A1 | 8/2005 | Chen |
| 2005/0288775 A1 | 12/2005 | Dong |
| 2007/0021841 A1 | 1/2007 | Al-Temen et al. |
| 2007/0078324 A1 | 4/2007 | Wijisiriwardana |
| 2009/0216339 A1 | 8/2009 | Hanson et al. |
| 2010/0114238 A1 | 5/2010 | Muccio |
| 2011/0230747 A1 | 9/2011 | Rogers et al. |
| 2011/0251469 A1 | 10/2011 | Varadan |
| 2012/0035435 A1* | 2/2012 | Choi ....................... A61B 5/282 600/301 |
| 2012/0126199 A1 | 5/2012 | O'Brien et al. |
| 2012/0296445 A1 | 11/2012 | Leiniger |
| 2013/0041235 A1 | 2/2013 | Rogers et al. |
| 2013/0046394 A1 | 2/2013 | Lipschutz et al. |
| 2013/0093287 A1 | 4/2013 | Biso et al. |
| 2013/0248163 A1 | 9/2013 | Bhagwagar et al. |
| 2014/0005763 A1 | 1/2014 | Cederna et al. |
| 2014/0025183 A1 | 1/2014 | Kelley |
| 2014/0039292 A1* | 2/2014 | Su ........................... A61B 5/276 600/372 |
| 2014/0148916 A1 | 5/2014 | Laghi et al. |
| 2014/0343390 A1* | 11/2014 | Berzowska ............. A61B 5/01 29/842 |
| 2015/0087951 A1* | 3/2015 | Felix ....................... A61B 5/25 600/382 |
| 2015/0335288 A1 | 11/2015 | Toth et al. |
| 2016/0158034 A1 | 6/2016 | Laghi et al. |
| 2016/0194792 A1 | 7/2016 | Satharasinghe et al. |
| 2018/0296822 A1 | 10/2018 | Schroeder |

FOREIGN PATENT DOCUMENTS

| | | |
|---|---|---|
| WO | 2014/197822 A2 | 12/2014 |
| WO | 2016007090 A1 | 1/2016 |
| WO | 2016/019250 A1 | 2/2016 |
| WO | 2019032118 A1 | 2/2019 |

OTHER PUBLICATIONS

Pomono Electronics Catalog, vol. 54, 92 pages (Jul. 2015).
European Patent Office, European Search Report and Search Opinion, European Patent Application No. 17920618.0, 7 pages (dated Apr. 23, 2020).
European Patent Office, Communication Pursuant to Article 94(3) EPC (Examination Report), European Patent Application No. 17920618.0, 6 pages (dated Nov. 27, 2020).
International Search Report and Written Opinion issued in PCT application No. PCT/US2017/046513 dated Dec. 14, 2017.
European Patent Office, Communication Pursuant to Article 94(3) EPC (Examination Report), European Patent Application No. 17920618.0, 6 pages (dated Apr. 12, 2021).
Partial European Search Report in European Patent Application No. 20172782.3, dated Sep. 30, 2020 (10 pages).
(EP) European Patent Office, Search Report and Search Opinion, European Patent Application No. 17859260.6, 9 pages, Apr. 23, 2020.
(PCT) U.S. Patent and Trademark Office (ISA/US), International Search Report, International Application No. PCT/US2017/055538, 2 pages, dated Dec. 28, 2017.
(PCT) U.S. Patent and Trademark Office (ISA/US), Written Opinion of the International Searching Authority, International Application No. PCT/US2017/055538, 6 pages, dated Dec. 28, 2017.
(US) U.S. Patent and Trademark Office, Non-Final Office Action, U.S. Appl. No. 15/726,624, 8 pages, dated Mar. 17, 2021.
(US) U.S. Patent and Trademark Office, Non-Final Office Action, U.S. Appl. No. 16/402,555, 14 pages, dated Apr. 6, 2020.
(US) U.S. Patent and Trademark Office, Final Office Action, U.S. Appl. No. 16/402,555, 12 pages, dated Oct. 29, 2020.
(US) U.S. Patent and Trademark Office, Advisory Action, U.S. Appl. No. 16/402,555, 3 pages, dated Apr. 29, 2021.
International Preliminary Report on Patentability in PCT/US2017/046513 dated Feb. 20, 2020.
U.S. Patent and Trademark Office, Final Office Action, U.S. Appl. No. 15/726,624, 10 pages, dated Sep. 30, 2021.
U.S. Patent and Trademark Office, Notice of Allowance, U.S. Appl. No. 16/402,555, 9 pages, dated Sep. 3, 2021.

* cited by examiner

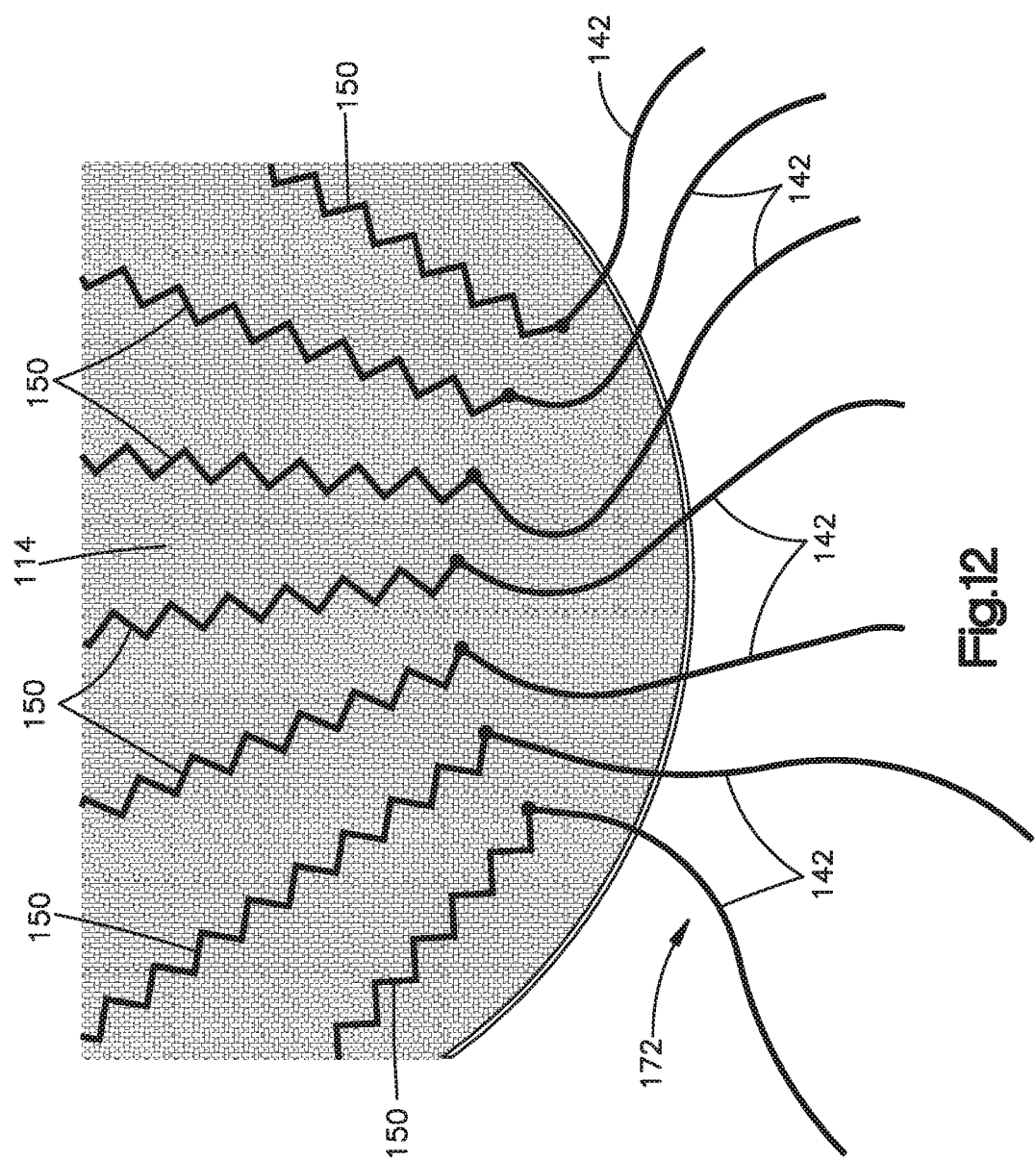

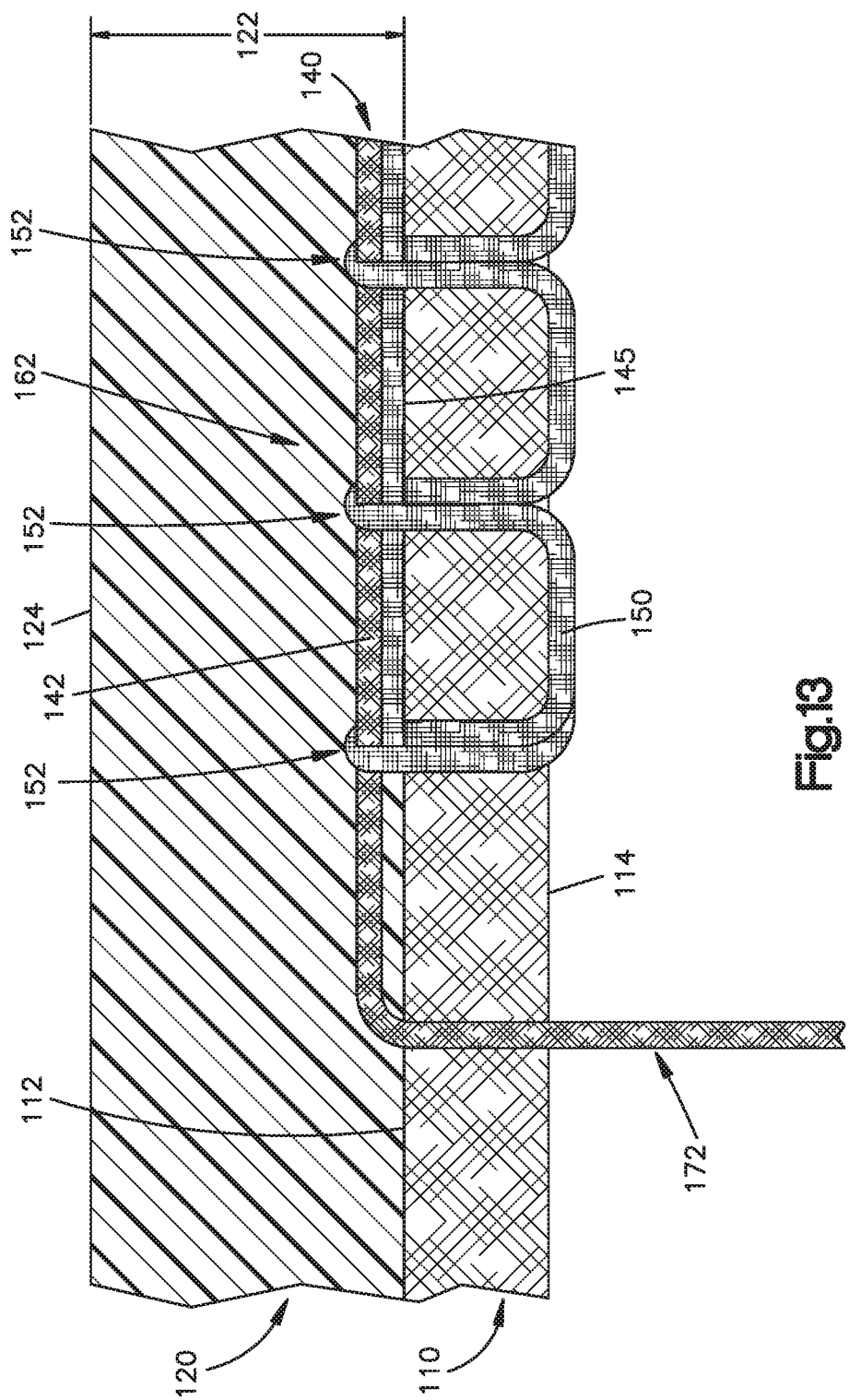

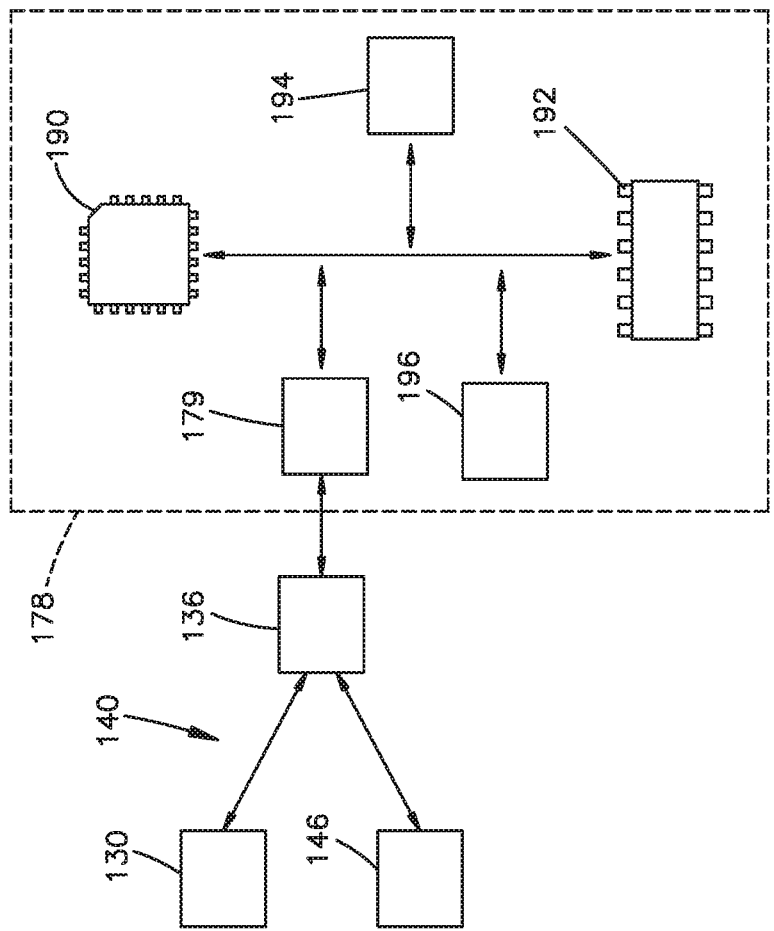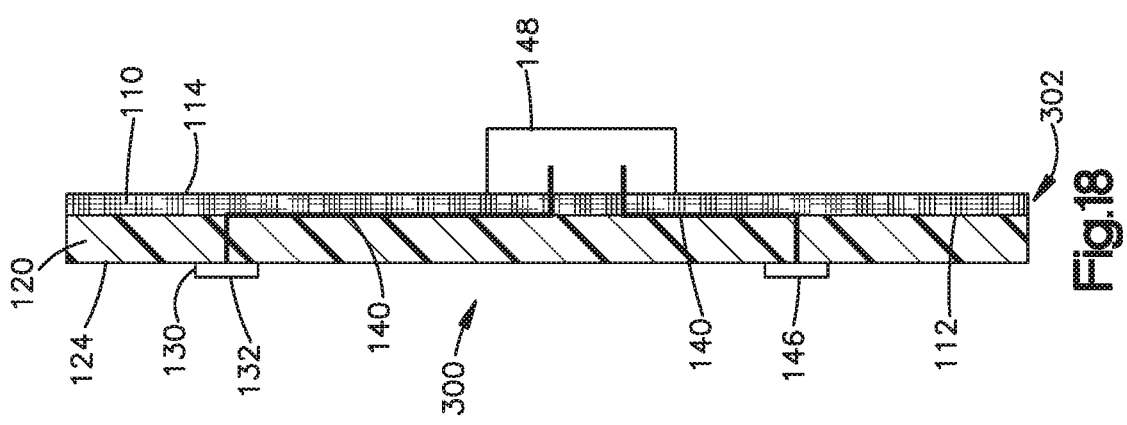

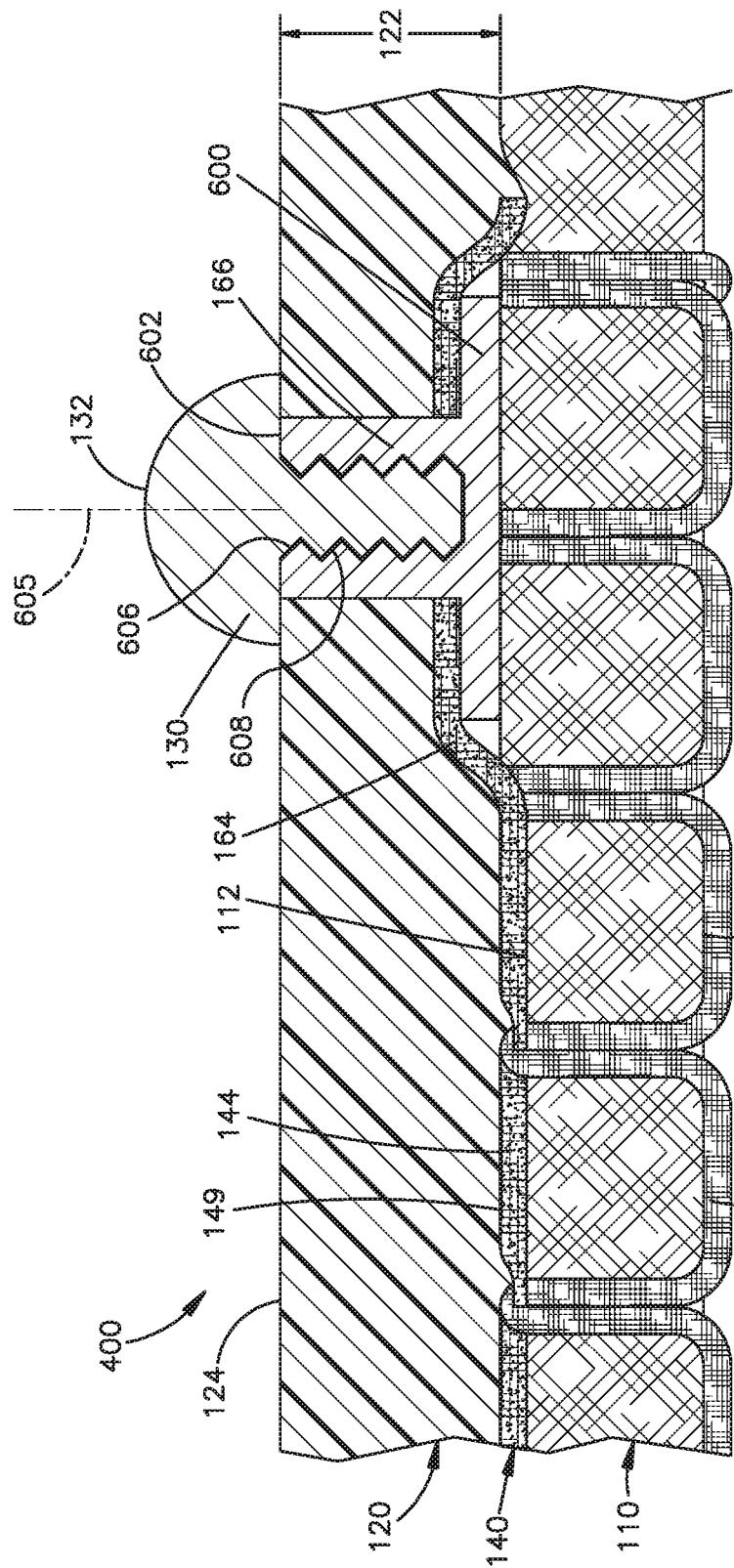
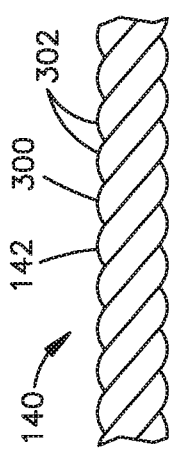
Fig.21
Fig.20

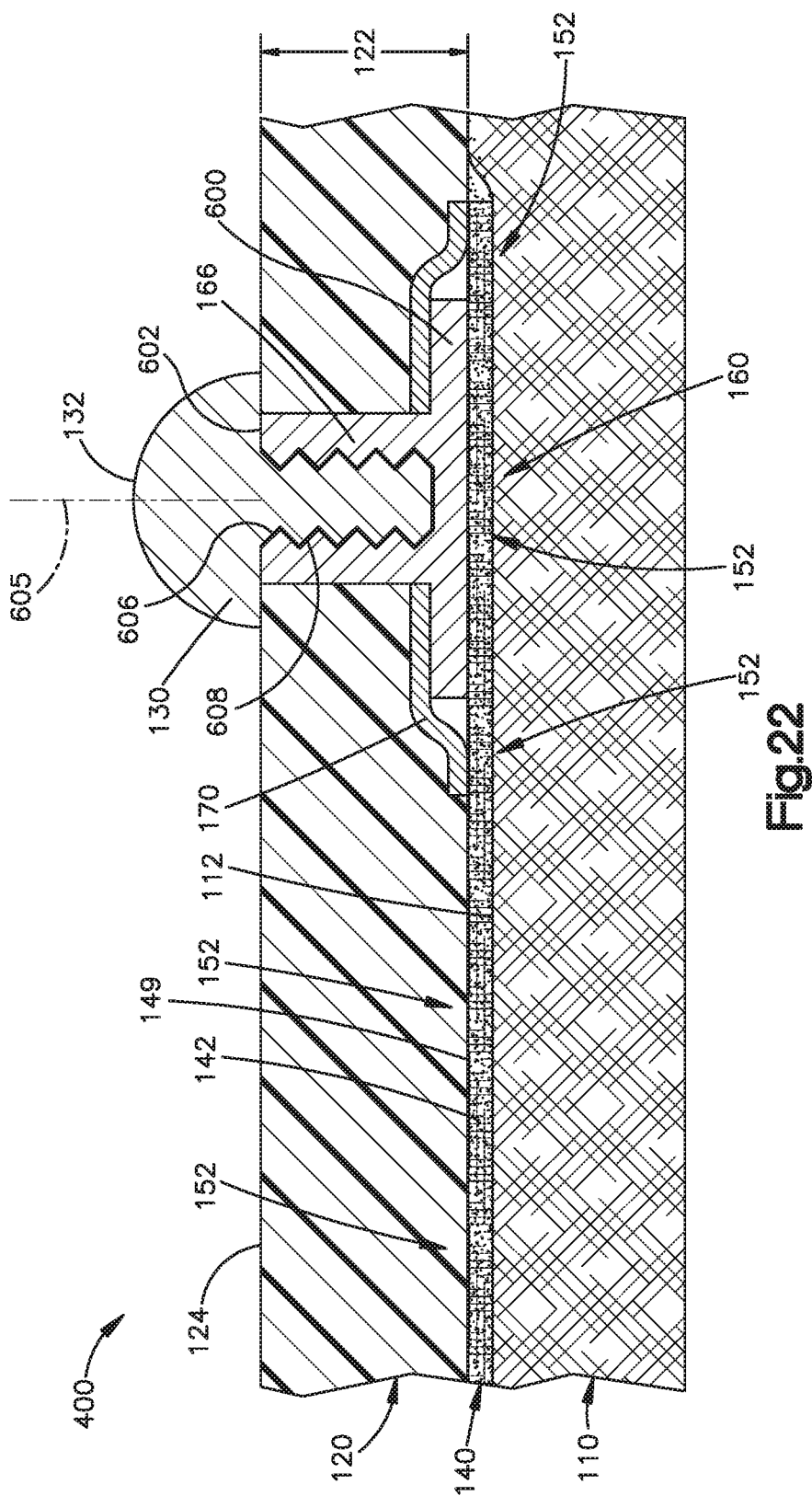

CONDUCTIVE HUMAN INTERFACES

RELATED APPLICATIONS

This application claims the benefit of provisional U.S. patent application 62/373,670, filed Aug. 11, 2016, which is incorporated by reference.

TECHNICAL FIELD

This technology includes conductive human interfaces for transmitting signals between a device and a user of the device, such as electromyographic signals that are transmitted from a user, and transcutaneous electrical nerve stimulation signals that are transmitted to a user.

BACKGROUND

Electromyographic (EMG) signals are relatively low powered electrical signals, in the range of about 10 µV to about 1 mV, that are generated in muscle tissue during contraction. Control of assistive devices using EMG signals can increase the functionality and the ease of use for a number of devices. For example, instead of requiring hand or body control of an assistive device such as a prosthetic, the EMG signals can be detected and used as input for the control of the device.

The low power of EMG signals can be detected by interfaces that place electrodes upon the skin of the user. Generally, additional electrical components are needed to process or amplify the EMG signals in order to generate signals suitable for control input. Thus, the EMG signals must be communicated from the detection site to the electrical components.

SUMMARY

A conductive human interface has a fabric layer with an interior surface and an exterior surface. A soft coating overlies the interior surface of the fabric layer. An electrode is included to connect with a residual limb. A conductive path connects the electrode with an electrical connector which, in turn, connects with a prosthetic device or other assistive device. The conductive path includes a conductor having a section overlying the fabric layer. The overlying section of the conductor can be cord of conductive thread. A support thread can extend through the fabric layer from the exterior surface to the interior surface, and further around the conductor to secure the overlying section of the conductor to the fabric layer.

The cord of conductive thread can have a monofilament structure, or can alternatively have a multi-filament structure of filaments that are bundled, spun or twisted together. A filament can be formed of nonconductive material that is coated or embedded with electrically conductive elements, or can alternatively be formed of conductive material, such as stainless steel.

Other embodiments can include alternative conductors such as, for example, conductive fabric and conductive ink.

The overlying section of the conductor can have an extendable length portion. In given examples, the extendable length portion has a first end, a second end spaced from the first end at a linear distance in a stretchable direction, and a length greater than the linear distance. The greater length enables the conductor to elongate in the stretchable direction when the fabric layer stretches in the stretchable direction. The electrode connector can have a base that is elongated in the stretchable direction.

In a given example, the conductive human interface is associated with a socket having a socket opening for insertion of a liner. The liner is configured to take an operative position in which a distal end portion of the liner is received in the socket, and a proximal end portion of the liner projects outward from the socket opening. An electrode or sensor is mounted on the proximal end portion of the liner, and is configured to electrically connect with a residual limb. An electrical connector is configured to electrically connect the electrode or sensor with a prosthetic device. A conductive path is configured to connect the electrode or sensor with the electrical connector. The conductive path reaches through the socket opening from the proximal end portion of the liner to the distal end portion when the liner is in the operative position.

A method of assembling the conductive human interface can include the step of removing the support thread from the fabric layer. In such cases the support thread is preferably dissoluble for removal by dissolving in a solvent such as water.

Another method of assembly may omit the support thread, and instead secure the conductor to the liner with an adhesive bond. The adhesive bond can be removed, preferably by dissolving in water.

BRIEF DESCRIPTION OF THE DRAWINGS

FIG. 12 depicts a closed end of a fabric layer.

FIG. 13 depicts an alternative embodiment of the structures shown in FIGS. 3-5.

FIG. 18 is a sectional view taken on line 18-18 of FIG. 17.

FIG. 19 schematically depicts a processing board.

FIG. 20 is an enlarged partial view of a conductor shown FIG. 3.

FIG. 21 depicts another alternative embodiment of the structures shown in FIGS. 3-5 and 13.

FIG. 22 depicts the structure of FIG. 21 in different condition.

DETAILED DESCRIPTION

Figure 1:
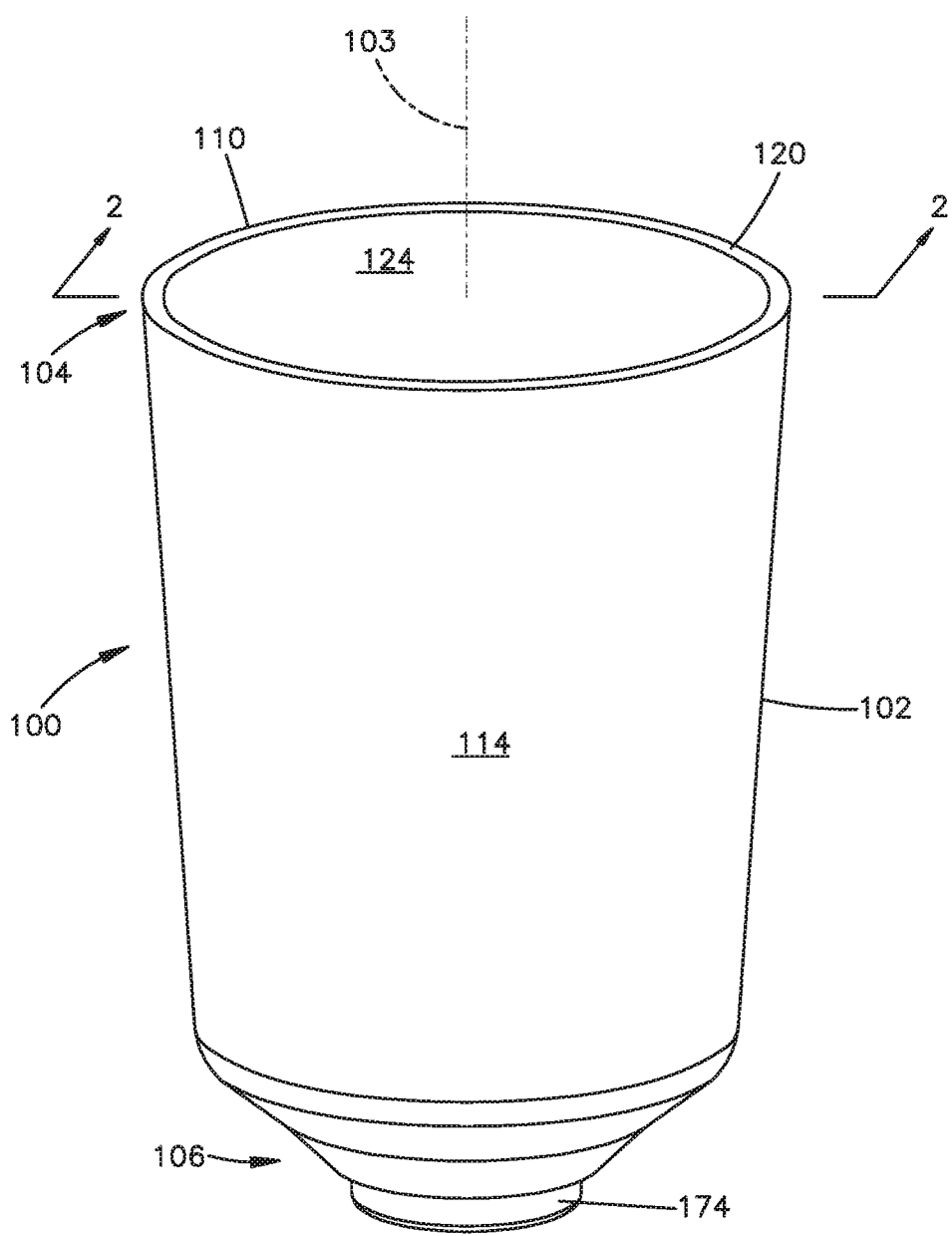
FIG. 1 depicts a conductive human interface.

The structures illustrated in the drawings include examples of the elements recited in the claims. The illustrated structures thus include examples of how a person of ordinary skill in the art can make and use the claimed invention. These examples are described to meet the enablement and best mode requirements of the patent statute without imposing limitations that are not recited in the claims. One or more elements of an embodiment may be used in combination with, or as a substitute for, one or more elements of another embodiment as needed for any particular implementation of the invention.

Figure 2:
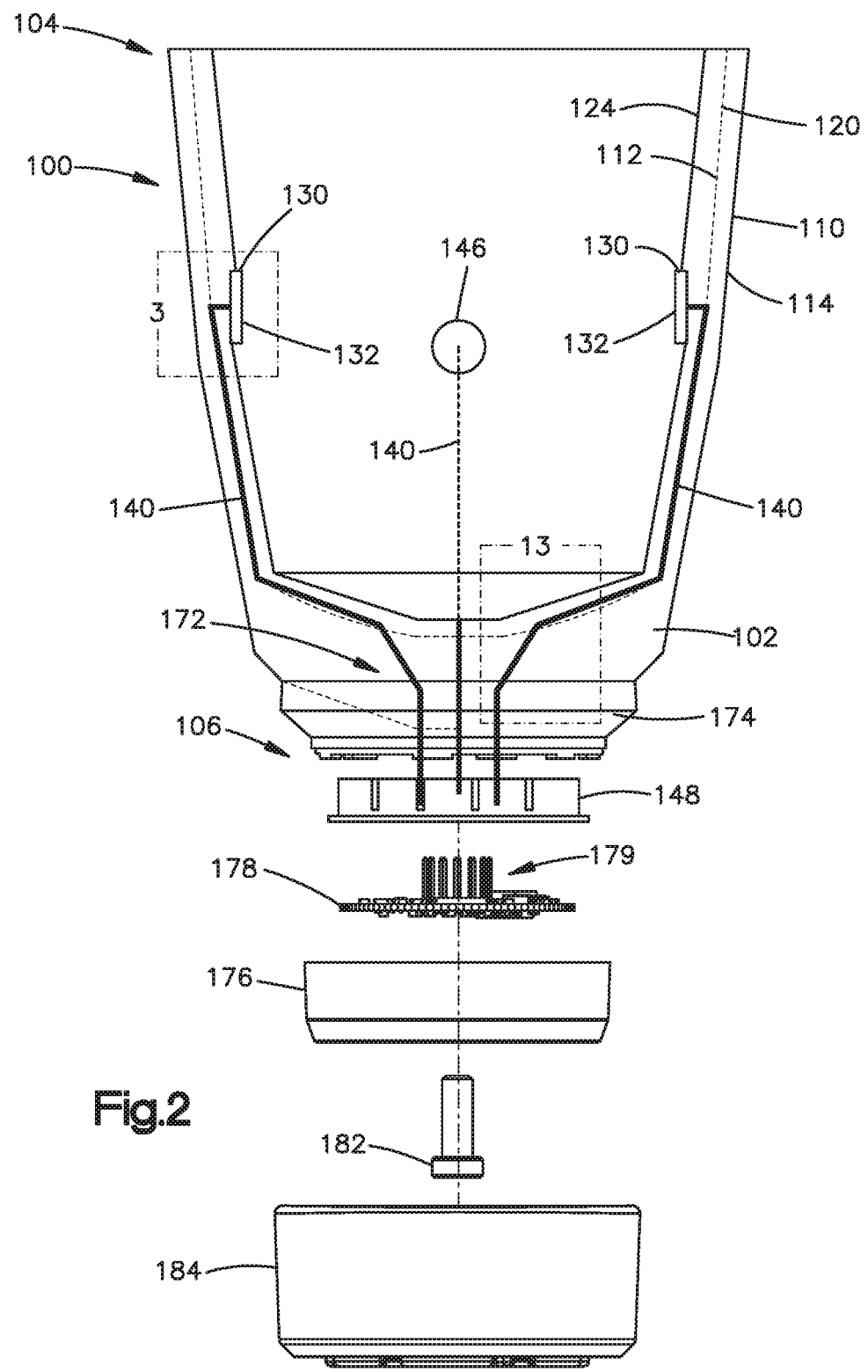
FIG. 2 depicts an exploded view of an interface system including a partial cross-sectional view of the conductive human interface of FIG. 1 along line 2-2.

Referring now to FIGS. 1 and 2, an embodiment of a conductive human interface 100 is schematically depicted. This example of a conductive human interface 100 is configured to capture electrical signals from the skin of a user and act as a physical interface with the user. In some embodiments, the conductive human interface 100 can also be configured to interface with an assistive device. The assistive device can be any device supplemental to the body of a user that cooperates with the neuromuscular and skeletal system of the user such as, for example, a prosthetic device (e.g., a prosthetic socket), an orthotic device, an exoskeletal device, a powered wheelchair, or the like. Accordingly, while certain embodiments of the present disclosure relate to a prosthetic liner 102 as shown in FIG. 1, the conductive human interface 100 can include the prosthetic liner 102, a sleeve, a band, a pad, or the like.

The conductive human interface 100 in the illustrated example includes a fabric layer 110 configured to form a flexible substrate. The fabric layer 110 can include one or more fabric materials such as, for example, stretch controlling fabrics, stretchable non-woven materials, fiber-on-end fabrics, or the like. Stretch-controlling fabric can be more stretchable in one direction than another direction. For example, a stretch-controlling fabric can have a limited stretch direction that is substantially orthogonal to a non-limited stretch direction. Accordingly, when the conductive human interface 100 includes a prosthetic liner 102, the stretch-controlling fabric can be oriented to permit greater stretch in a circumferential direction than in a longitudinal direction (i.e., along the length of the prosthetic liner 102 in the direction of the longitudinal axis 103).

Figure 3:
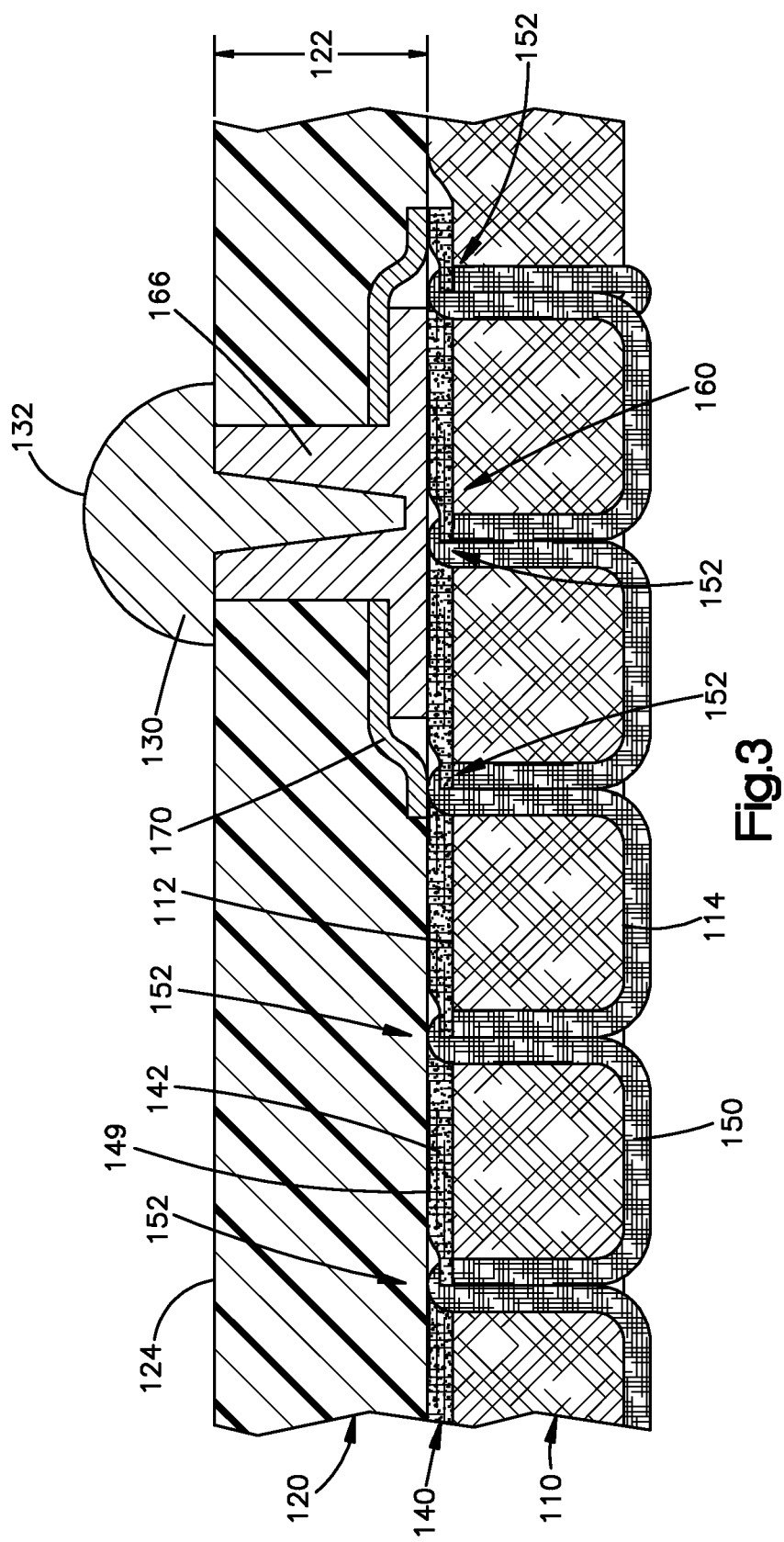
FIG. 3 is an enlarged partial view 3 of structure shown in FIG. 2.

Referring now to FIG. 3, the fabric layer 110 can include an interior surface 112 and an exterior surface 114. The interior surface 112 can form a boundary with a soft coating 120 configured for comfortable long term wear. The soft coating 120 can be formed from materials having a hardness on the Shore 00 scale such as, for example, a hardness of less than about 75 on the Shore 00 scale in one embodiment, or a hardness of between about 15-35 on the Shore 00 scale in another embodiment. Accordingly, the soft coating 120 can be formed from a soft polymer such as, for example, thermoplastic elastomers (TPE), silicones, block copolymers, urethanes, or the like. The thickness 122 of the soft coating 120, as measured from the interior surface 112 of the fabric layer 110 to the contact surface 124 of the soft coating 120, can be less than about 1 inch such as, for example, less than about 0.75 inches in one embodiment, or between about 0.150 and about 0.50 inches.

Referring to FIGS. 2 and 3, the conductive human interface 100 includes one or more electrodes 130 configured to make contact with the skin of the user and to receive EMG signals produced by muscles of the user. Generally, the electrodes 130 can be formed from conductive material such as, for example, metal or a polymeric material impregnated with conductive particles such as, for example, silicone impregnated with carbon particles. The electrodes 130 can be substantially even with the contact surface 124 of the soft coating 120 or protrude beyond the contact surface 124 of the soft coating 120. Each electrode 130 includes a detection surface 132 shaped to promote electrical contact with the skin of the user. For example, the detection surface 132 can be domed shaped, as shown for example in FIG. 3, or substantially flat, corrugated or any other shape or surface treatment that promotes electrical conductivity with the skin.

Referring to FIGS. 2-5, the conductive human interface 100 further includes a conductive path 140 for electrically connecting each electrode 130 to another component. As used herein, the phrase "electrically connect" means to provide a medium for the transmission of electrical signals from one object to another object. The conductive path 140 generally includes a flexible conductor such as, for example, conductive thread 142 (FIG. 3), conductive fabric 144 (FIG. 4), a conductive ink 145 (FIG. 5), or combinations thereof. A section 149 of each conductor 142, 144, or 145 overlies the interior surface 112 of the fabric layer.

The conductive thread 142 (FIG. 3) is configured as a cord with either a monofilament structure or a multi-filament structure. A conductive filament can be formed of a conductive material, such as stainless steel, and alternatively could be formed of a non-conductive substrate material that is coated or embedded with electrically conductive elements such as, for example, silver, carbon, nickel, copper, gold, titanium, or the like. Substrates can include cotton, polyester, nylon, aramids, or the like. A multi-filament structure can be formed from a plurality of conductive filaments that are bundled, spun or twisted together into a substantially cord-like shape. In some embodiments, the conductive thread 142 can be formed from multiple plys of thread that are spun or twisted together into a substantially cord-like shape such as, for example, 2 plys in one embodiment, or 4 plys in another embodiment. The conductive thread 142 can be characterized by linear resistance. In some embodiments, the conductive thread 142 can have a linear resistance of less than about 10 Ω/in such as, for example, less than about 6 Ω/in in one embodiment, between about 0.5 Ω/in to about 3.5 Ω/in in another embodiment. The conductive thread 142 can also be characterized by linear density. In some embodiments, the conductive thread 142 can have a linear density of at least about 2,000 yd/lb such as, for example, between about 3,000 yd/lb and about 9,500 yd/lb in one embodiment, between about 3,500 yd/lb and about 4,000 yd/lb in another embodiment, or between about 8,500 yd/lb and about 9,000 yd/lb in another embodiment.

In distinction from the cord of the conductive thread 142, the conductive fabric 144 (FIG. 4) can be a substantially sheet like material formed from a plurality of conductive filaments or conductive threads 142 that are woven, knitted, or bonded together via chemical, mechanical, heat or solvent treatments. The conductive ink 145 (FIG. 5) can be a conductive body formed from a conductive liquid that has been dried, cured, cooled or a combination thereof. The conductive ink 145 can include electrically conductive elements, as described above, suspended within a substrate (e.g., polymer film).

Referring again to FIG. 2, the conductive human interface 100 can include one or more sensors 146 configured to detect physical characteristics of the conductive human interface 100, the skin of the user, or both. The one or more sensors 146 can be electrically connected to the conductive path 140 in a manner similar to the electrical connection of the electrodes 130, as described in greater detail below. It is noted that the term "sensor," as used herein, can mean a device that measures a physical quantity and converts it into an electrical signal, which is correlated to the measured value of the physical quantity. A sensor 146 can thus comprise a temperature sensor, a moisture sensor, a gyroscope, shear sensor, pressure sensor, force sensor (e.g., normal force, sliding force), distance sensor, or combinations thereof. At least a portion of the one or more sensors can be embedded within the soft coating 120. Alternatively or additionally, the sensor 146 can include a power source, processor, or both located external to the conductive human interface 100. For example, the components of the sensor 146 can be electrically connected via the conductive path 140.

Figure 7:
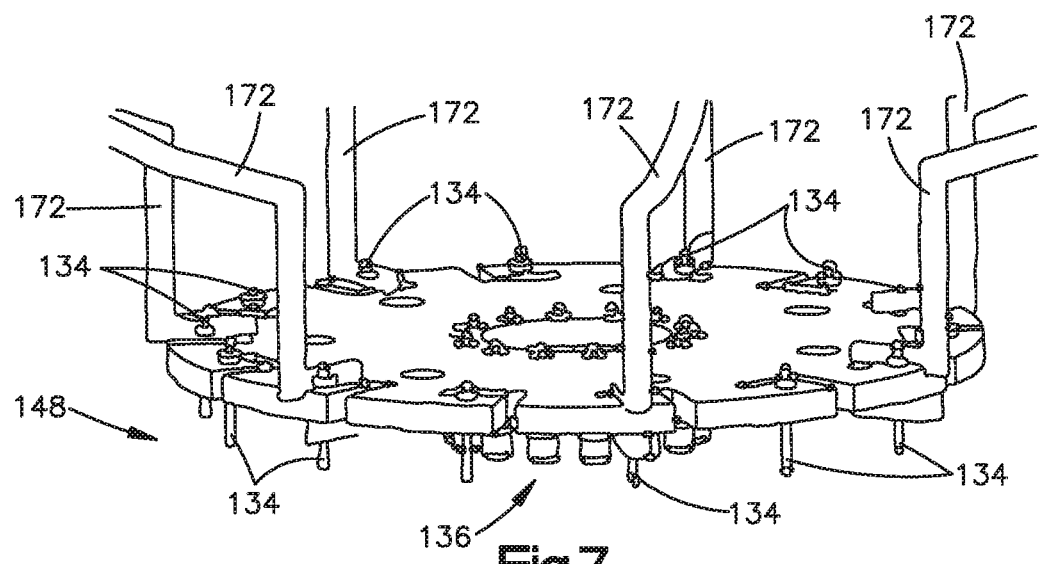
FIG. 7 is a perspective view an electrical connector.

Referring to FIGS. 2 and 7, the conductive human interface 100 can include an electrical connector 148 configured to electrically connect each conductive path 140 with another component. The electrical connector 148 can include conductive members 134 (FIG. 7), each of which is configured to be electrically connected to one of the conductive paths 140. Specifically, a conductive member 134 can include features configured to provide a mechanical connection with fabric or thread. For example, the conductive member 134 can include a feature that promotes a knotted connection such as, but not limited to, a slot (e.g., "L" shaped slot), a boat cleat shaped member, a knob, a hook, orifices, or the like. Accordingly, an electrical connection can be formed by wrapping a portion (e.g., a connector lead 172) of the conductive path 140 around the conductive member 134, tying the portion of the conductive path 140 to the conductive member 134 or combinations thereof. In some embodiments, the electrical connector 134 can be configured to transition from relatively flexible conductors to more rigid conductors. For example, the electrical connector 148 can include a separable electrical connector 136 (e.g., pins, sockets, etc.) electrically connected to the conductive members 134.

Referring to FIGS. 2 and 3, a method for forming the conductive human interface 100 can include providing the fabric layer 110 in the desired shape such as, for example, as a panel, a tube, or a sock. In embodiments where the fabric layer 110 is shaped into a sock (FIG. 2), the conductive human interface 100 can be provided as a prosthetic liner 102 configured to serve as an interface between a residual limb and a prosthetic socket. Accordingly, the prosthetic liner 102 can extend between an open end 104 and a closed end 106.

The conductive path 140 can be attached to the fabric layer 110. In embodiments where the conductive path 140 includes conductive thread 142, the conductive thread 142 can be stitched to the fabric layer 110 using a support thread 150 (FIG. 3), which can be non-conductive. For example, one of the conductive thread 142 and the support thread 150 can be provided in the thread feed of a sewing machine, and the other can be provided in the bobbin. Accordingly, a majority of the conductive thread 142 can be located on the interior surface 112 of the fabric layer 110. Additionally, a majority of the support thread 150 can be located on the exterior surface 114 of the fabric layer 110.

The tension applied at each of the needle punctures 152 through the fabric layer 110 can be controlled to improve the flexibility of the conductive path 140. For example, flexibility of the conductive path 140 can be improved by having the support thread 150 loop around the conductive thread 142 inwards above the interior surface 112 of the fabric layer 110 as shown, for example, in FIG. 3. That is, the support thread 150 can be pushed completely through the fabric layer 110 and separated from the interior surface 112 of the fabric layer 110 by the conductive thread 142 at the needle puncture 152. Accordingly, the conductive thread 142 can be held to the interior surface 112 of the fabric layer 110 by the support thread 150, which can be provided both on the interior surface 112 and the exterior surface 114 of the fabric.

Figure 9:
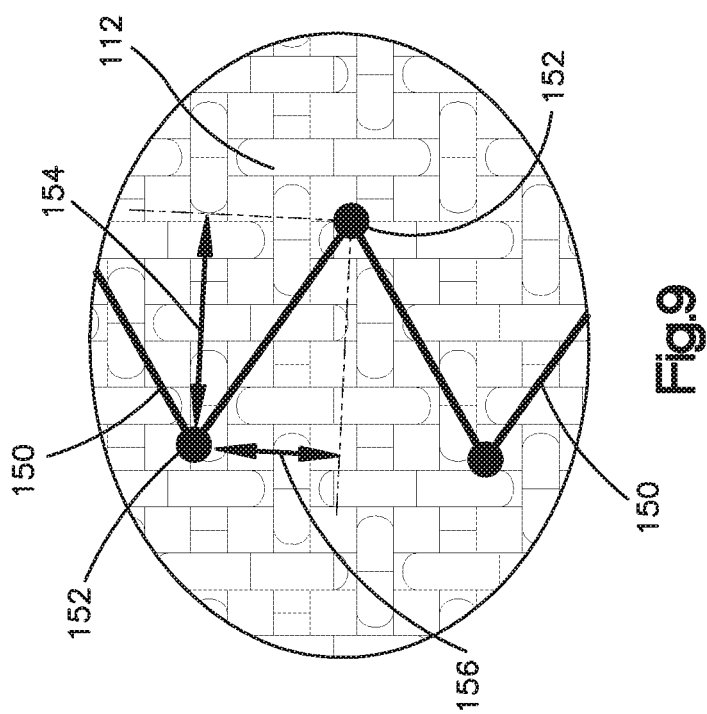
FIGS. 8 and 9 depict conductive paths.
Figure 8:
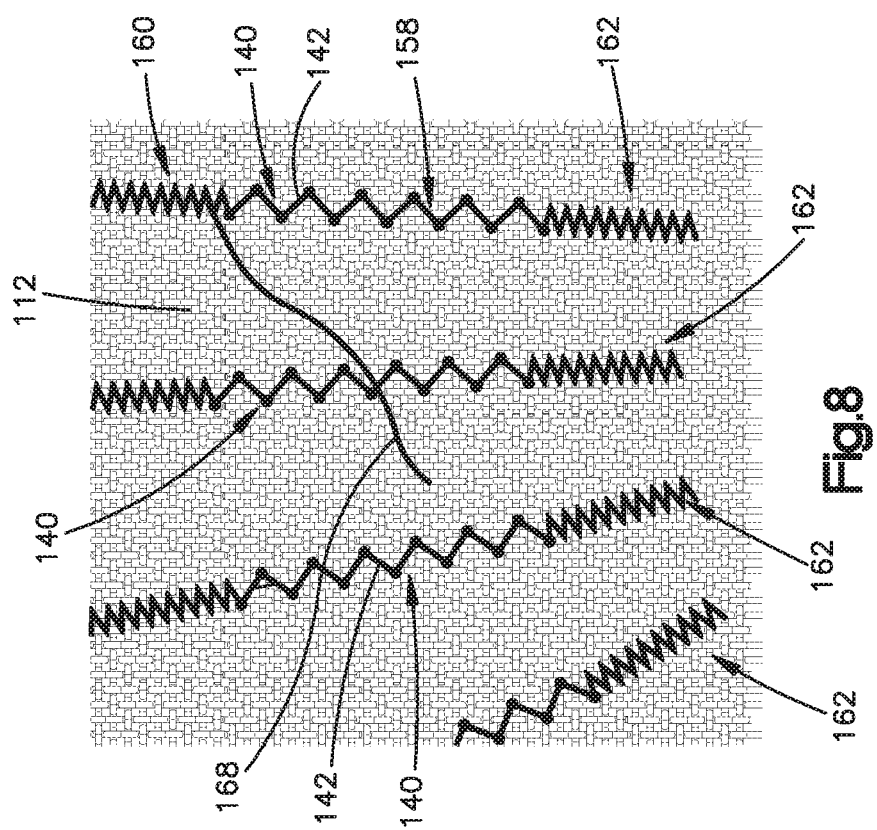

Referring to FIGS. 8 and 9, in embodiments where the conductive path 140 includes conductive thread 142, the durability of the conductive path 140 can be improved by controlling the aspect ratio along the conductive path 140. The aspect ratio can be determined by dividing a width 154 between adjacent needle punctures 152 by a length 156 between the adjacent needle punctures 152. Preferably, the aspect ratio can be greater than about 1 such as, for example, greater than about 1.1 in one embodiment, greater than about 1.25 in another embodiment, or about 1.5 in a further embodiment. Generally, the length 156 refers to a direction substantially parallel to the overall direction in which the conductive path 140 is elongated between its opposite ends, and the width 154 refers to a direction substantially orthogonal to the length. Further improvements can be provided by aligning the length 156 between punctures 152 along the length of the prosthetic liner 102. In embodiments where the conductive thread 142 is stitched with a machine, the direction the fabric layer 110 is fed through the machine can define the direction of the conductive path 140.

The conductive thread 142 can include a span 158 (FIG. 8) formed between an electrode patch 160 and a connector patch 162. The electrode patch 160 and the connector patch 162 can be configured to anchor the conductive path 140. In some embodiments, the aspect ratio of the conductive thread 142 at the electrode patch 160 and the connector patch 162 can be greater than the aspect ratio of the conductive thread 142 of the span 158. For example, the aspect ratio of the conductive thread 142 at the electrode patch 160 and the connector patch 162 can be at least twice as large as the aspect ratio of the conductive thread 142 of the span 158 such as, for example, at least about four times as large.

Additionally, manufacturability of the conductive human interface 100 can be improved by overlapping multiple layers of the conductive thread 142 at the electrode patch 160, the connector patch 162, or both. For example, the layers can be overlapped to form a patch 160 or 162 by taking multiple passes over the same location. In embodiments where the conductive thread 142 is stitched with a machine, the feed direction can be reversed back and forth over the location of the electrode patch 160, the connector patch 162, or both to provide the number of layers desired to form the patch 160 or 162 at that location. Additionally, changing the feed direction can cause the conductive thread 142 to self-knot or self-entangle, which can improve the overall durability of the conductive path 140 and reduce manufacturing time. Accordingly, the electrode patch 160, the connector patch 162, or both can include more layers than the span 158. In some embodiments, the electrode patch 160 can include a greater number of layers of the conductive thread 142 than the connector patch 162.

Figure 4:
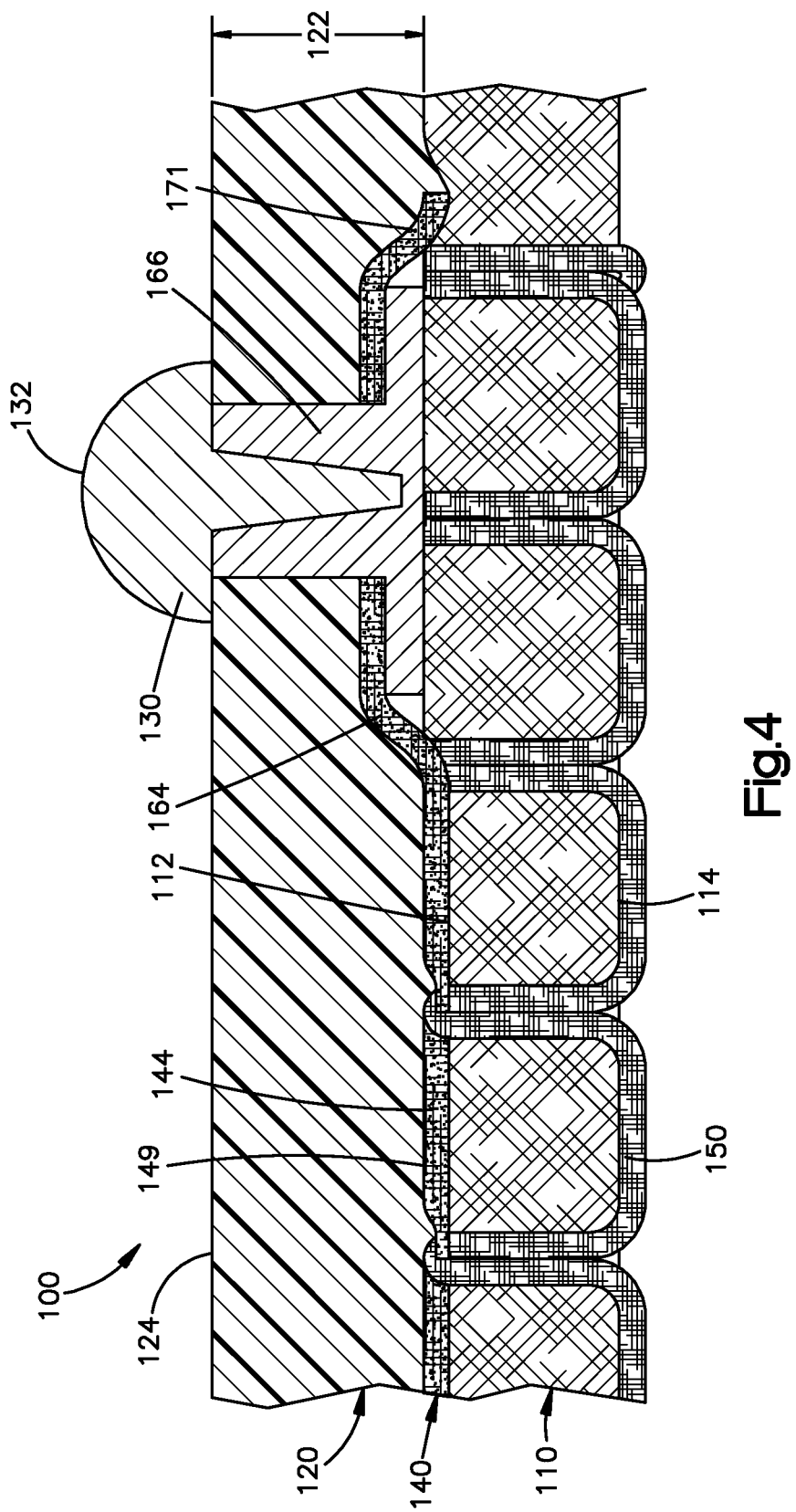
FIGS. 4 and 5 depict alternative embodiments of the structure shown in FIG. 3.
Figure 6:
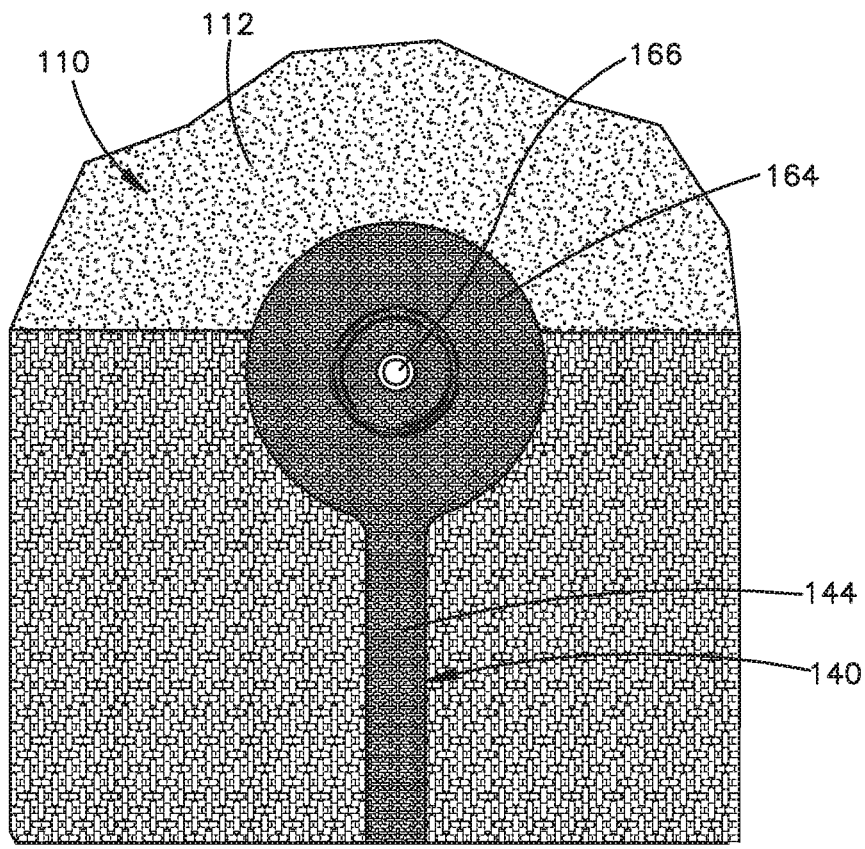
FIG. 6 is an enlarged partial view of the conductive human interface of FIG. 2.

Referring to FIGS. 4 and 6, in embodiments where the conductive path 140 includes conductive fabric 144, the conductive fabric 144 can be attached to the interior surface 112 of the fabric layer 110 such as, for example, with adhesive, stitching, or the like. In some embodiments, the conductive fabric 144 can be cut to a shape that is configured to extend between an electrode 130 and the electrical connector 148. The shape of the conductive fabric 144 can include an electrode portion 164 configured to be attached to the electrode 130. Accordingly, the electrode portion 164 can be correspondingly shaped to the electrode 130. In embodiments where the conductive path 140 includes conductive ink 145, the conductive ink 145 can be applied directly to the interior surface 112 of the fabric layer 110.

Referring to FIGS. 3-6 and 9-10, a method for forming the conductive human interface 100 can include electrically connecting an electrode connector 166 to the conductive path 140. The electrode connector 166 can be formed from conductive materials such as, for example, a metal (e.g., copper, aluminum, gold, silver, etc.), a graphite material, or a conductive polymer. In embodiments where the conductive path 140 includes conductive thread 142, the electrode patch 160 can be configured to electrically connect with the electrode connector 166. For example, the conductive thread 142 of the electrode patch 160 can define a conductive region at the interior surface 112 of the fabric layer 110 for promoting electrical contact with the electrode connector 166.

Additionally, the electrode connector 166 can be configured to mechanically connect to the conductive path 140 and the electrode 130. The electrode connector 166 can include one or more features that promote a knotted connection, as described above, with an electrode lead 168 (FIGS. 8 and 9) extending from the electrode patch 160. Accordingly, the electrode lead 168 can be wrapped or tied to the features of the electrode connector 166, which can improve the contact between the electrode connector 166 and the electrode patch 160.

Figure 10:
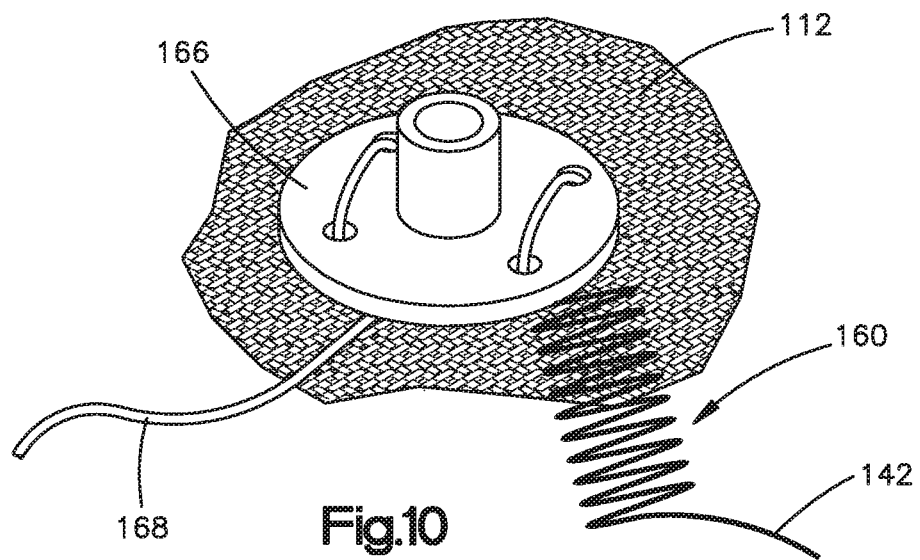
FIGS. 10-11 depict an electrode connector and a conductive path.

Alternatively or additionally, a fabric patch 170 can be used to provide a mechanical connection between the electrode connector 166 and the electrode patch 160, as best shown in FIG. 10. In some embodiments, the fabric patch 170 can cover the electrode connector 166 and can be adhered to the interior surface 112 of the fabric layer 110. Accordingly, the electrode connector 166 can be positioned between the fabric patch 170 and the interior surface 112 of the fabric layer 110 as shown in FIG. 3. Moreover, the fabric patch 170 can be configured to isolate the electrical connection between the electrode patch 160 and the electrode connector 166 from the soft coating 120. For example, when the fabric patch 170 is applied before the soft coating 120, undesired intrusion of the soft coating 120 between the electrode connector 166 and the electrode patch 160 can be mitigated. Accordingly, the mechanical and electrical connection can be improved.

Referring to FIGS. 4 and 6, in embodiments where the conductive path 140 includes conductive fabric 144, the electrode connector 166 can be electrically and mechanically connected with the electrode portion 164 of the conductive fabric 144. For example, the electrode portion 164 can partially cover the electrode connector 166 and extend beyond the electrode connector 166. The overhanging portion 171 of the electrode portion 164 can be adhered to the interior surface 112 of the fabric layer 110. Thus, the electrode connector 166 can be positioned between the electrode portion 164 of the conductive fabric 144 and the interior surface 112 of the fabric layer 110.

Figure 5:
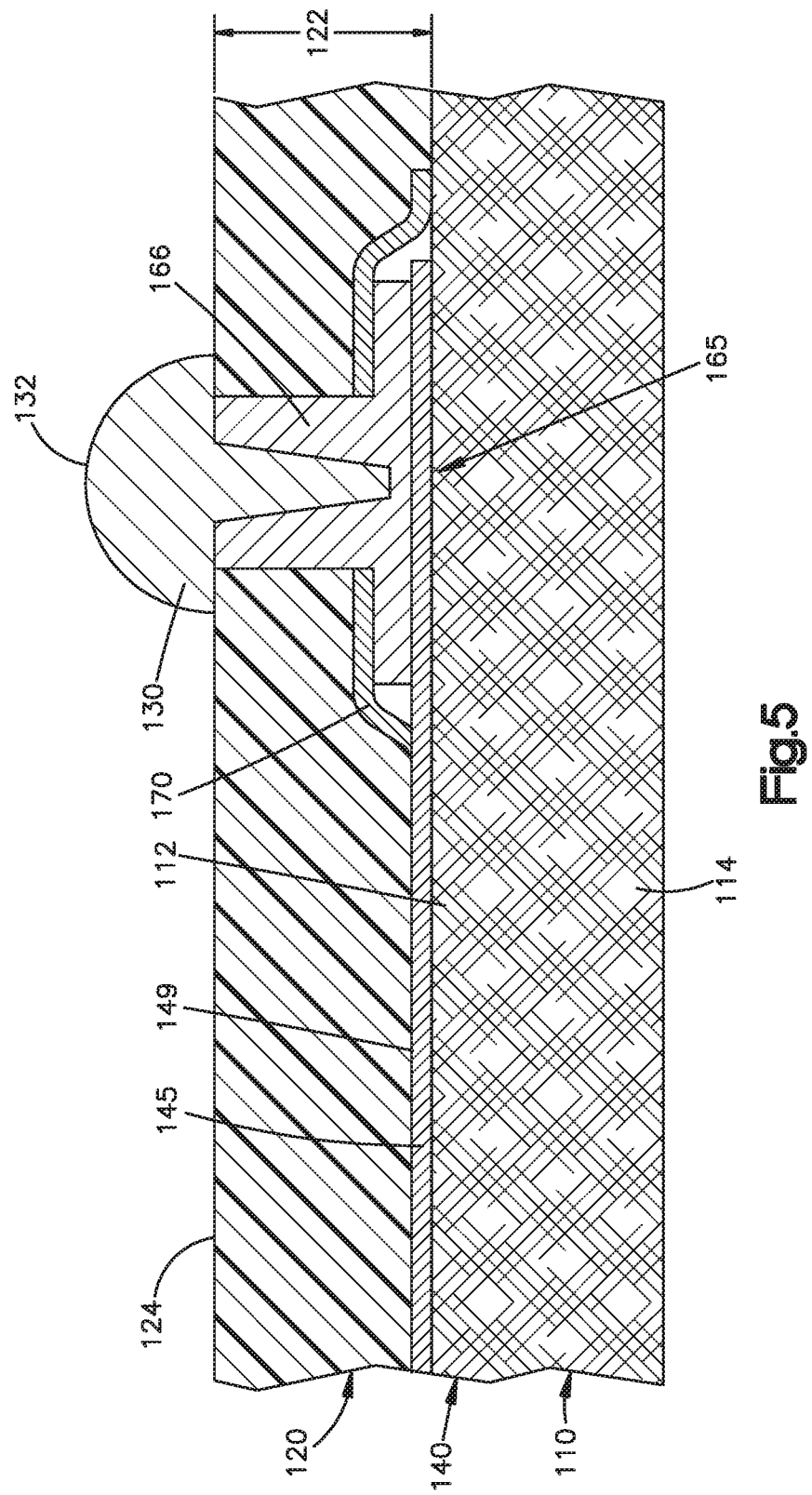

Referring to FIGS. 2 and 5, in embodiments where the conductive path 140 includes conductive ink 145, the electrode connector 166 can be electrically and mechanically connected with the electrode portion 165 of the conductive ink 145. For example, the electrode portion 165 can be applied directly to the interior surface 112 of the fabric layer 110 such that the electrode portion 165 is at least as large as the electrode connector 166. The conductive ink 145 can be cured prior to connecting with the electrode connector 166. Alternatively, the electrode connector 166 can be connected to the electrode portion 165, while the conductive ink 145 is in an uncured state. Accordingly, the curing process can contribute to the quality of the connection therebetween. Alternatively or additionally, the fabric patch 170 can be used to isolate and improve the mechanical connection and the electrical connection between the electrode connector 166 and the electrode portion 165, as noted above. Specifically, the electrode connector 166 can be positioned between the fabric patch 170 and the electrode portion 165 of the conductive ink 145. Additionally, the fabric patch 170 can substantially cover the electrode portion 165, such that the fabric patch 170 is adhered to the interior surface 112 of the fabric layer 110 around the electrode portion 165.

Figure 11:
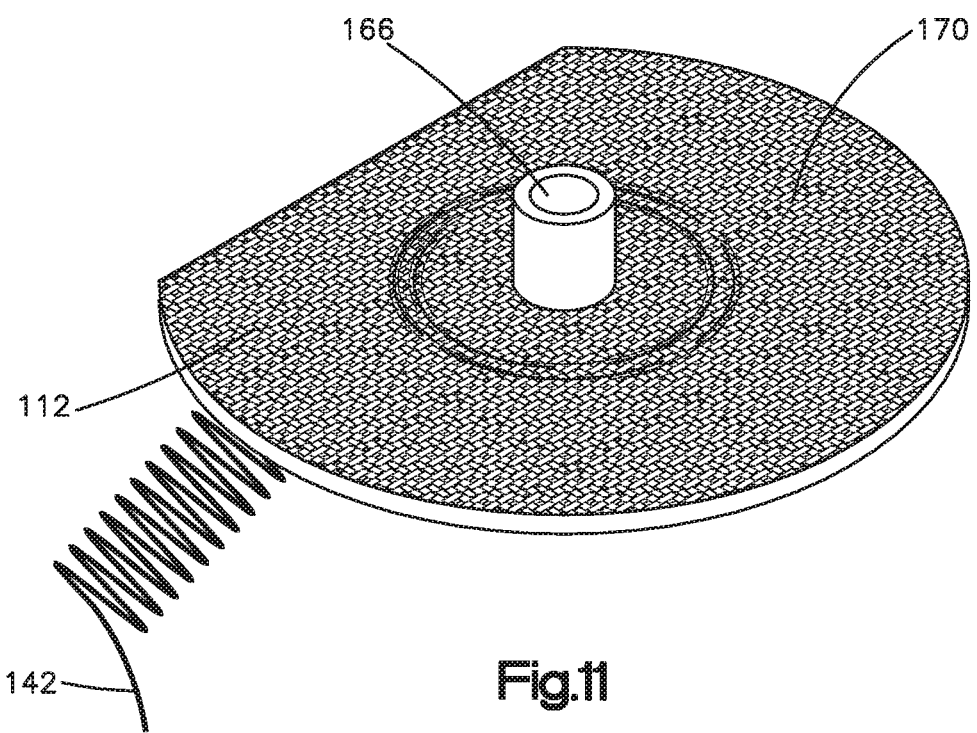

Referring to FIGS. 11 and 12, a method for forming the conductive human interface 100 can include arranging connector leads 172 with respect to the fabric layer 110. In some embodiments, the conductive path 140 can include connector leads 172 that extend beyond the exterior surface 114 of the fabric layer 110. The connector leads 172 can be formed from the conductive thread 142, the conductive fabric 144, conductive ink 145 applied to a non-conductive fabric, or combinations thereof. A connector lead 172 can extend from the connector patch 162 and through one or more orifices in the fabric layer 110 as shown, for example, in FIG. 13. For example, in embodiments where the conductive human interface 100 includes the prosthetic liner 102, the connector leads 172 can extend through the fabric layer 110 at the closed end 106.

In embodiments where the conductive path 140 includes conductive ink 145, the conductive ink 145 can be electrically connected to the connector lead 172 at the connector patch 162. For example, the conductive ink 145 can be applied to the interior surface 112 of the fabric layer 110. After the conductive ink 145 is applied, the connector patch 162 can be stitched upon the conductive ink 145 with the conductive thread 142. Accordingly, each of the needle punctures 152 can be formed through the conductive ink 145 and the connector lead 172 can be formed with conductive thread 142. In embodiments where the connector lead 172 is formed of the conductive fabric 144 or the conductive ink 145 applied to a non-conductive fabric, the connector lead 172 can be applied over the conductive ink 145 and the fabric of the connector lead 172 can be adhered to the interior surface 112 of the fabric layer 110. Accordingly, the conductive ink 145 can be positioned between the connector lead 172 and the interior surface 112 of the fabric layer 100.

In alternative embodiments, the conductive ink 145 can be applied over the connector lead 172, i.e., the connector lead 172 can be positioned between the conductive ink 145 and the interior surface 112 of the fabric layer 100. For example, the connector lead 172 can be formed from conductive thread 142 and the conductive ink 145 can be applied over the connector patch 162. In embodiments where the connector lead 172 is formed of the conductive fabric 144 or the conductive ink 145 applied to a non-conductive fabric, the conductive ink 145 can be applied over the connector lead 172.

In a method for forming the conductive human interface 100, the soft coating 120 can be applied in a gel state and cured within a mold to form the soft coating 120. In some embodiments, the soft coating 120 can be applied after the conductive path 140 is formed upon the fabric layer 110. Accordingly, the conductive path 140 can be covered by or embedded within the soft coating 120. In embodiments, where the connector leads 172 extend through the fabric layer 110, the orifices in the fabric layer 110 can be sized such that the connector leads 172 are compressed in the fabric layer 110. For example, each orifice can be smaller than the connector leads 172 that pass through the orifice. Thus, the orifices can be configured to mitigate permeation of the soft coating 120.

The electrode connector 166 can include one or more features that promote a mechanical connection with the electrode 130 such as, for example, a threaded connection, a friction fit, a clamping feature, a pin connector, a socket connector, or the like. Thus, while the electrode connector is depicted in FIG. 6 as a metal tee nut, the embodiments provided herein are not so limited. Accordingly, the electrode 130 can be connected to the electrode connector 166 after the soft coating 120 is applied to the fabric layer 110.

The electrode connector 166 can be configured to protrude away from the interior surface 112 of the fabric layer 110. For example, the feature for connecting with the electrode 130 can be offset from the interior surface 112 of the fabric layer 110. In embodiments with the fabric patch 170, the feature for connecting with the electrode 130 can protrude through the fabric patch 170. Accordingly, the electrode connector 166 can at least partially extend through the soft coating 120 and can mate with the electrode 130 after the soft coating 120 is applied to the fabric layer 110.

In embodiments where the electrodes 130 are formed from polymeric materials, the electrodes 130 can be applied directly to the conductive path 140 (e.g., the electrode patch 160, the electrode portion 164, or the electrode portion 165). Accordingly, the electrodes 130 can make surface contact with the conductive path 140 or both the conductive path 140 and the interior surface 112 of the fabric layer 110. In some embodiments, the polymeric material can be applied directly to the conductive path 140 in a gel state and cured to form the electrode 130. The direct contact allows for the electrode connector 166 to be omitted in certain embodiments. In some embodiments, the polymeric material of the electrodes 130 can be applied before the soft coating 120 is applied. Alternatively, the polymeric material of the electrodes 130 can be applied after the soft coating 120 is applied. For example, a removable body can cover the electrode sites on the conductive path 140, while the soft coating 120 is applied. The removable body can then be removed to allow the polymeric material of the electrodes 130 to be applied to the electrode sites.

Referring to FIGS. 2 and 7, a method for forming the conductive human interface 100 can include electrically connecting the conductive path 140 to the electrical connector 148. Specifically, each of the connector leads 172 can be electrically and mechanically connected to one of the conductive members 134 as shown, for example, in FIG. 7. Accordingly, the signals can be communicated by each of the conductive paths 140 to an assistive device in communication with the separable electrical connector 136.

Referring again to FIGS. 1 and 2, the prosthetic liner 102 can include an umbrella 174 formed at the closed end 106 and external to the exterior surface 114 of the fabric layer 110. In some embodiments, the umbrella 174 can be formed around the electrical connector 148. For example, the umbrella 174 can be molded to the exterior surface 114 of the fabric layer 110 out of relatively hard materials such as, for example, a hard urethane. Accordingly, the connector leads 172 can extend through the fabric layer 110 at the closed end 106 of the prosthetic liner 102 above the umbrella 174.

Figure 14:
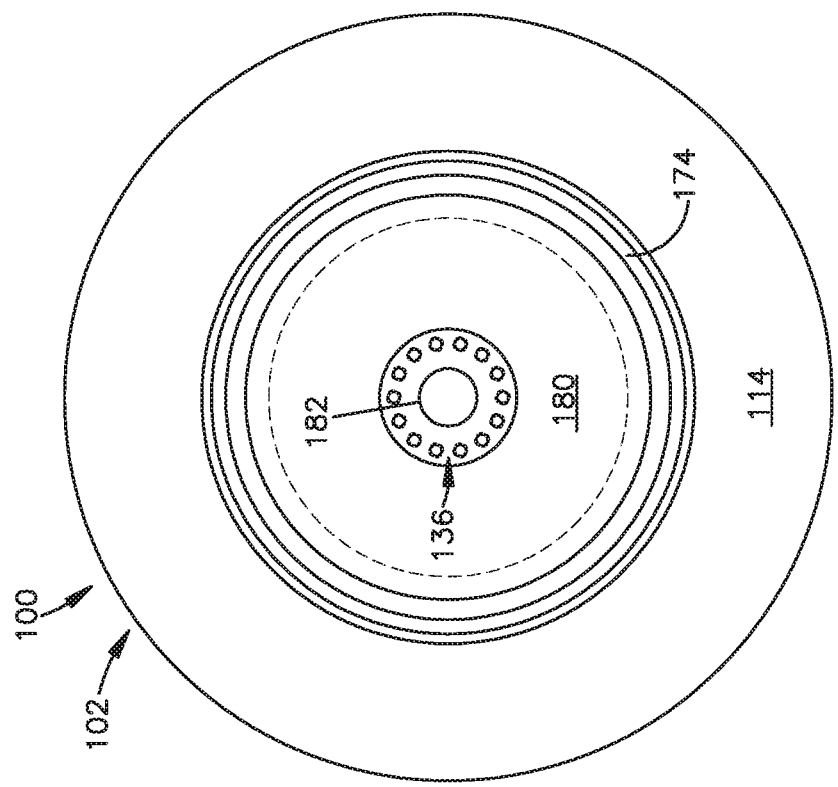
FIG. 14 depicts an umbrella of a liner.

The umbrella 174 can be configured to electrically connect with a proximal interface 176 (FIG. 2). Specifically, the umbrella 174 can be correspondingly shaped to the proximal interface 176. The proximal interface 176 can include a processing board 178 configured to electrically connect with the separable electrical connector 136 (FIG. 7) of the electrical connector 148. For example, the processing board 178 can include a separable electrical connector 179 configured to connect with the separable electrical connector 136 of the electrical connector 148. In some embodiments, the separable electrical connector 136 of the electrical connector 148 can be at least partially revealed at a face 180 (FIG. 14) of the umbrella 174.

The umbrella 174 can be configured to mechanically connect with the proximal interface 176. For example, a fastener 182 (e.g., threaded coupling) can be provided on the face 180 of the umbrella 174. It is noted that, the prosthetic liner 102 may deteriorate more rapidly than the components (e.g., signal processors, microprocessors, memory, battery, etc.) of the processing board 178 of the proximal interface 176. Accordingly, the proximal interface 176 can be reused when the prosthetic liner 102 needs to be replaced.

The proximal interface 176 in the illustrated example is configured to be coupled and decoupled with a distal interface 184 (FIG. 2) on a daily basis. The distal interface 184 can be attached to a prosthetic socket. Each of the distal interface 184 and the proximal interface 176 can include magnetic members that are configured to form a magnetic coupling therebetween. Additionally, the distal interface 184 and the proximal interface 176 can be configured to be decoupled by relative rotation which displaces the magnetic members from one another. An additional clamping member can be provided to selectively retain the distal interface 184 and the proximal interface 176 in alignment to promote the magnetic coupling.

Figure 15:
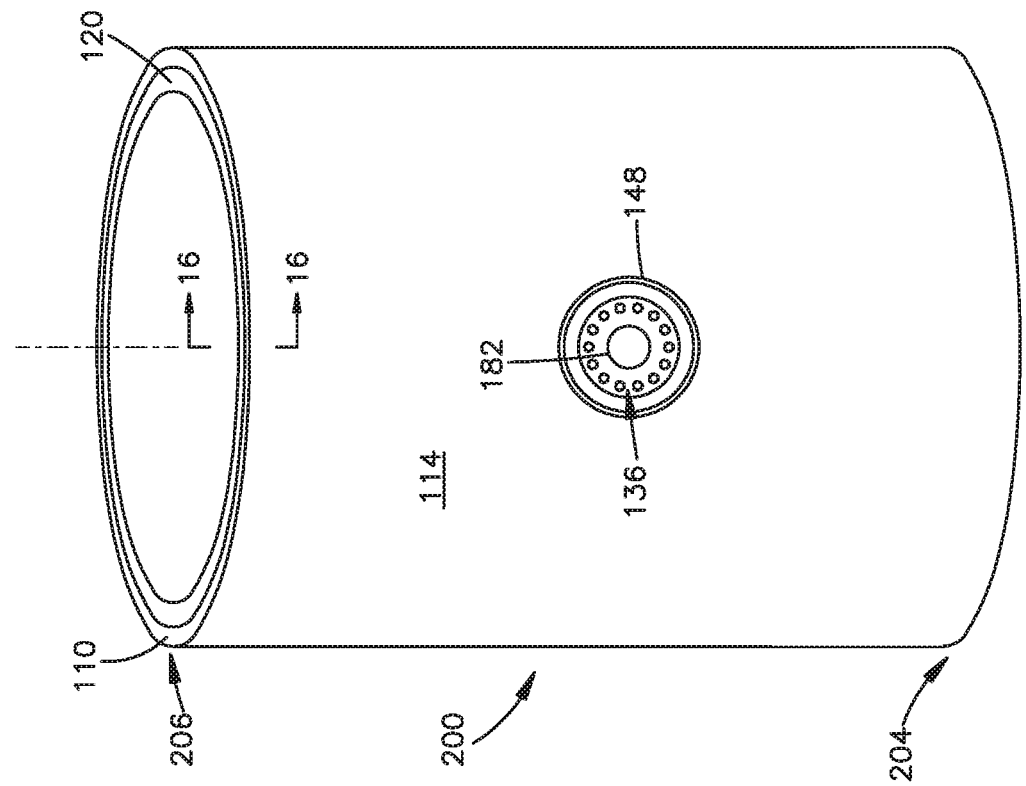
FIG. 15 depicts an alternative embodiment of a conductive human interface.
Figure 16:
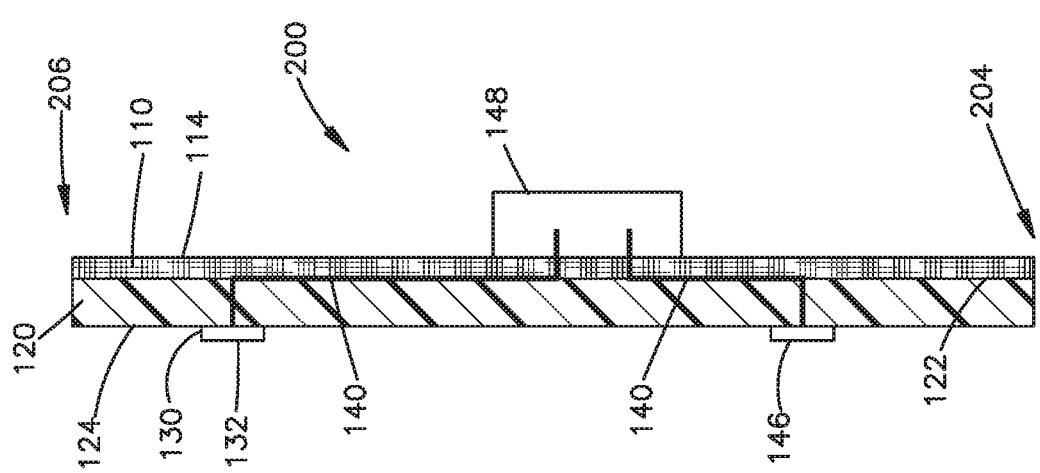
FIG. 16 is a sectional view taken on line 16-16 of FIG. 15.

Referring FIGS. 15 and 16, an embodiment of a conductive human interface 200 can be substantially tubular. For example, the conductive human interface 200 can extend between a first open end 204 and a second open end 206. Accordingly, the conductive human interface 200 can be provided as, for example, an arm sleeve, a leg sleeve, a wrist band, a head band, or the like. Generally, the conductive human interface 200 can include the fabric layer 110, the soft coating 120, the electrode 130, the sensor 146, and the electrical connector 148, as described herein with respect to the conductive human interface 100. Additionally, the conductive human interface 200 can be formed in substantially the same way as the conductive human interface 100. In some embodiments, the electrical connector 148 can be provided on the exterior surface 114 of the fabric layer 110 between the first open end 204 and the second open end 206. Alternatively, the electrical connector 148 can be provided at the first open end 204, the second open end 206, or both.

Figure 17:
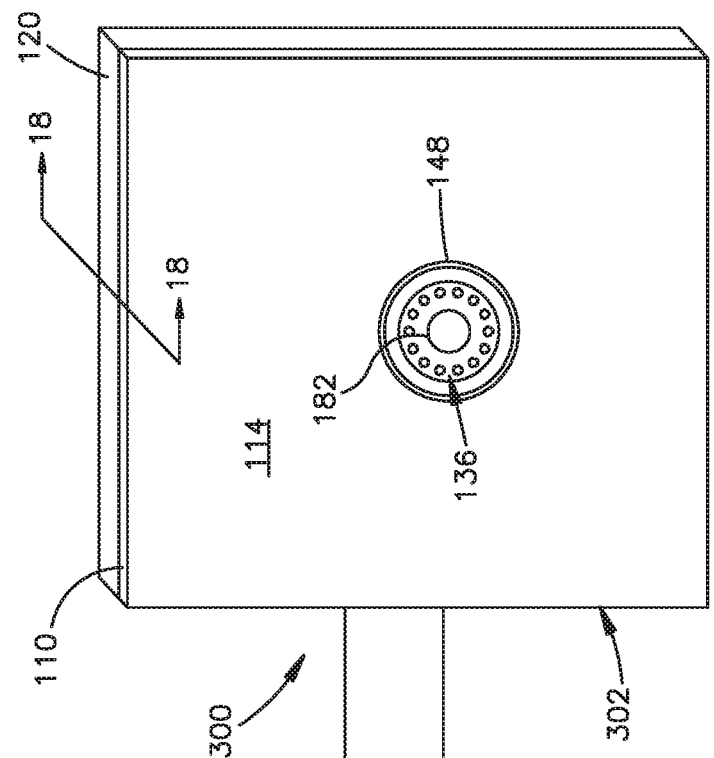
FIG. 17 depicts another alternative embodiment of a conductive human interface.

Referring to FIGS. 17 and 18, an embodiment of a conductive human interface 300 can be formed as a substantially sheet shaped body. For example, the conductive human interface 300 can have a thickness that is defined by the fabric layer 110 and the soft coating 120 and demarcated by a perimeter 302. It is noted that, while the perimeter 302 is depicted in FIG. 17 as being substantially rectangular, the perimeter can be contoured to match with any desired body part. Optionally, the conductive human interface 300 can include a band 304 configured to wrap around a user and secure the conductive human interface 300 to the desired body part. Generally, the conductive human interface 300 can include the fabric layer 110, the soft coating 120, the electrode 130, the sensor 146, and the electrical connector 148, as described herein with respect to the conductive human interface 100. In some embodiments, the electrical connector 148 can be provided on the exterior surface 114 of the fabric layer 110. Additionally, the conductive human interface 300 can be formed in substantially the same way as the conductive human interface 100.

Referring to FIGS. 2 and 19, the processing board 178 can be operable to communicate electrical signals with the electrode 130, the sensor 146, or both. The processing board 178 can include one or more processors 190 for executing machine readable instructions to perform signal communication functions, as described herein. The term "processor" can mean any device capable of executing machine readable instructions. Accordingly, each processor can be a controller, an integrated circuit, a microchip, a signal processor, or any other device capable of implementing logic. The processing board 178 can include memory 192 communicatively coupled to the one or more processors 190 (generally depicted as double arrowed lines). As used herein, the phrase "communicatively coupled" can mean that components are capable of exchanging data signals with one another such as, for example, electrical signals via conductive medium, electromagnetic signals via air, optical signals via optical waveguides, and the like. The memory 192 described herein may be RAM, ROM, a flash memory, a hard drive, or any device capable of storing machine readable instructions.

Additionally, it is noted that the functions described herein can be provided as machine readable instructions stored on the memory 192 and executed by the one or more processors 190. The machine readable instructions can be provided in any programming language of any generation (e.g., 1GL, 2GL, 3GL, 4GL, or 5GL) such as, e.g., machine language that may be directly executed by the processor, or assembly language, object-oriented programming (OOP), scripting languages, microcode, etc., that may be compiled or assembled into machine readable instructions and stored on a machine readable medium. Alternatively, the functions, modules, and processes described herein may be written in a hardware description language (HDL), such as logic implemented via either a field-programmable gate array (FPGA) configuration or an application-specific integrated circuit (ASIC), and their equivalents. Accordingly, the functions described herein may be implemented in any conventional computer programming language, as pre-programmed hardware elements, or as a combination of hardware and software components.

The processing board 178 can be configured to transform EMG signals detected by the electrode 130 into control signals for an assistive device. Alternatively or additionally, the processing board 178 can be configured to transform sensor signals communicated by the sensor 146 into control signals for an assistive device. For example, the separable electrical connector 179 can be communicatively coupled with the one or more processors 190. Additionally, the processing board 178 can include device communication hardware 194 communicatively coupled to the one or more processors 190. The device communication hardware 194 can be configured to communicate, i.e., send and/or receive data signals via any wired or wireless communication protocol such as, for example, LIN bus, CAN bus, USB, FIREWIRE, IrDA, BLUETOOTH, Wireless USB, Z-WAVE, ZIGBEE, or the like. Accordingly, the one or more processors 190 can receive signals via the separable electrical connector 179 and transform the signals into control signals. The control signals can then be transmitted via the device communication hardware 194 to the assistive device.

Additionally, the processing board 178 can be configured to transmit electrical signals to the electrode 130. For example, the electrical signals can be configured to stimulate nerve endings, create information flowing into the body, or both. In some embodiments, the processing board 178 can include a signal generator 196 configured to generate electrical signals that can be communicated to the electrode 130. For example, the signal generator 196 can be communicatively coupled to the separable electrical connector 179 and the one or more processors 190. Accordingly, the one or more processors 190 can cause the signal generator 196 to generate the desired electrical signal. The electrical signal can be transmitted to the electrode 130 via the conductive path 140 and the separable electrical connector 136. Alternatively, the electrical signals can be provided directly to the separable electrical connector 179 via the device communication hardware 194. Accordingly, in some embodiments, the signal generator 196 is omitted.

The electrical signals can configured for Transcutaneous electrical nerve stimulation (TENS). Thus, the electrode 130 can be aligned with the desired nerve ending to manage pain. For example, amputees can experience phantom limb pain, i.e., pain that is sensed as coming from an amputated limb. For example, nerve endings at the site of amputation can stimulate the brain in a manner that is interpreted as pain from the removed limb. Alternatively or additionally, the electrical signals can be transmitted to muscle or nerve endings as feedback from an assistive device. For example, amputees using assistive devices such as, for example, a prosthetic foot may have difficulty detecting uneven surfaces. Often times, the amputee may need to look directly at the assistive device in order to traverse an uneven surface. In some embodiments, the assistive device can be provided with sensors configured to detect the uneven surface such as, for example, load sensors to detect the amount and type of loading, and contact sensors configured to detect contact with the surface. In some embodiments, the sensor information can be communicated to the electrode 130 as feedback that can stimulate the brain. For example, the one or more processors 190 can receive sensor data and cause the signal generator 196 to generate the desired electrical signal. The one or more processors 190 can encoded the electrical signal according to the sensor data. Alternatively, the electrical signals can be provided directly to the separable electrical connector 179 via the device communication hardware 194.

As described above with reference to the embodiment of FIG. 3, the conductor 140 can be a cord of conductive thread 142 formed of conductive filaments that are spun or twisted together. An example of such a cord 300 is shown in greater detail in FIG. 20. The filaments 302 can include non-conductive substrate material that is coated or embedded with electrically conductive elements. The filaments 302 can alternatively be formed of conductive material such as, for example, stainless steel. In each case, the filaments 302 preferably have a Z twist for sewing, as shown in FIG. 20.

Another embodiment of a conductive human interface 400 is shown in FIGS. 21 and 22. Specifically, the conductive human interface 400 has a partially assembled condition as shown in FIG. 21, and has a more fully assembled condition as shown in FIG. 22.

In this embodiment, the conductive human interface 400 has many parts that correspond with parts of the conductive human interface 100 described above with reference to FIGS. 2 and 3. This is indicated by the use of the same reference numbers for such corresponding parts. The conductive human interface 400 thus includes a fabric layer 110 having an interior surface 112 and an exterior surface 114, with a soft coating 120 overlying the interior surface 112. An electrode 130 is configured to electrically connect with a residual limb. A conductive path 140 is configured to connect the electrode 130 with an electrical connector 148 (FIG. 2) which, in turn, is configured to electrically connect with a prosthetic device. The conductive path 140 includes a conductor 142 having a section 149 overlying the interior surface 112 of the fabric layer 110 between the soft coating 120 and the fabric layer 110.

In the partially assembled condition of FIG. 21, the conductive human interface 400 includes nonconductive support thread 150 extending through the fabric layer 110 from the exterior surface 114 to the interior surface 112. The support thread 150 extends further around the conductor 142 to secure the overlying section 149 of the conductor 142 to the fabric layer 110.

The conductive human interface 400 is advanced from the partially assembled condition of FIG. 21 to the more fully assembled condition of FIG. 22 by removing the support thread 150. The support thread 150 is preferably dissoluble for removal by dissolving in a solvent such as water. The needle punctures 152 and the inherent porosity of the fabric layer 110 may enable the solvent to penetrate from the exterior surface 114 of the fabric layer 110 sufficiently to dissolve the support thread 150 completely. Removing the support thread 150 provides the exterior surface 114 with a smoother contour and texture. At the interior surface 112, the overlying section 149 of the conductor 142 remains secured in the conductive path 140, but is released from the support thread 150 to enable a slight amount of shifting on the surface 112 as needed in response to forces imparted from the residual limb or the connected prosthetic device.

In an alternative method of assembly the support thread 150 can be omitted. Such a method could comprise the steps of connecting a conductor between an electrical connector and an electrode or sensor; placing a section of the conductor in a position overlying an interior surface of a fabric layer; forming an adhesive bond securing the overlying section of the conductor to the interior surface of the fabric layer; applying a soft coating over the interior surface of the fabric layer, the overlying section of the conductor, and portions of the support thread reaching around the conductor; and removing the adhesive bond.

In the foregoing method, the adhesive bond can be formed of a dissoluble adhesive material, and preferably a water-dissoluble adhesive material. The step of removing the adhesive bond would then comprise dissolving the adhesive bond, and more specifically dissolving the adhesive bond in water. A cornstarch mixture could serve as the water-dissoluble adhesive material.

Figure 23:
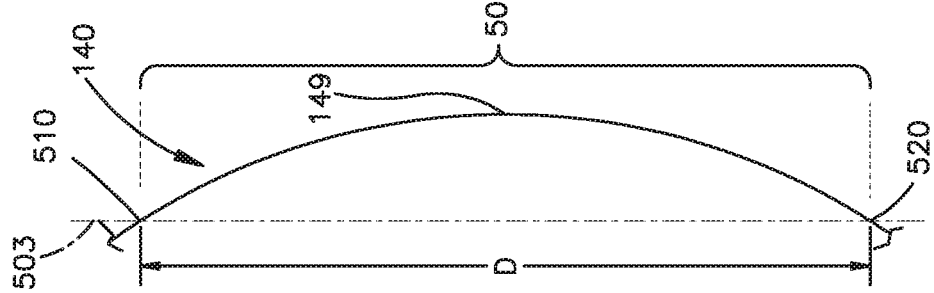

In each embodiment, the conductors 140 are preferably elongated lengthwise of the respective fabric layer. This is illustrated by the examples shown in FIGS. 8, 9, and 12, where the conductors 140 are shown to be elongated in directions either parallel or generally oriented in alignment with the length of the prosthetic liner 102 along the axis 103. In each case, the section 149 of the conductor 140 that overlies the fabric layer 110 has one or more extendable length portions 500, as shown for example in the schematic view of FIG. 23. The extendable length portion 500 is elongated in a longitudinal direction along an axis 503, and has a proximal end 510 and a distal end 520. The distal end 520 is spaced from proximal end 510 at a linear distance D in the longitudinal direction. However, the extendable length portion 500 itself is longer than the linear distance D between the opposite ends 510 and 520. The greater length enables the overlying section 149 of the conductor to 140 elongate in the longitudinal direction when the fabric layer stretches in the longitudinal direction.

Figure 24:
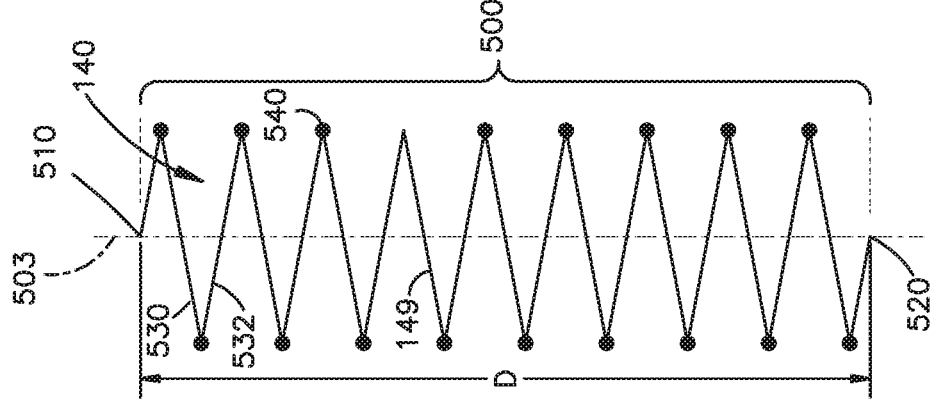

In the example shown schematically in FIG. 24, the extendable length portion 500 of the conductor 140 has first segments 530 and second segments 532. The first segments 530 reach distally in orientations laterally toward one side of the longitudinal direction. The second segments 532 alternate with the first segments 530, and reach distally in orientations laterally toward an opposite side of the longitudinal direction. As shown in 23, the alternating segments 530, 532 are linear and reach distally in a zig-zag configuration with corners 540 between adjacent segments 530, 532. In the example of FIG. 24, the alternating segments 530, 532 are arcuate and reach distally in a serpentine configuration with turns 550 between adjacent segments 530, 532. Although the illustrated examples are oriented for stretching in the longitudinal directions, the conductors could likewise have extendable length portions oriented for stretching in lateral or other stretchable directions.

Referring again to FIGS. 21 and 22, the electrode connector 166 has a base portion 600 and a column portion 602, both of which have circular cross-sectional shapes centered on an axis 605. The base 600 can be adhesively bonded to the interior surface 112 of the fabric layer 110. The base 600 can alternatively be adhesively bonded to the exterior surface 114, with the column 602 extending inward through the fabric layer 110. In that condition an electrically nonconductive cap, such as a body of polyurethane gel, would be received over the base 600.

The column 600 in this example has an internal screw-thread 606 for engaging an external screw thread 608 on the electrode 130. This enables the user to install electrodes 130 at fewer than all of the connectors 166, leaving the remaining connectors 166 free of electrodes 130 at the contact surface 124. The conductive human interface 400 is thus adaptable for a user to employ electrodes 130 at only selected locations on the residual limb, although other locations are also available as needed, and thereby to avoid discomfort where unnecessary electrodes 130 might be located.

Figure 26:
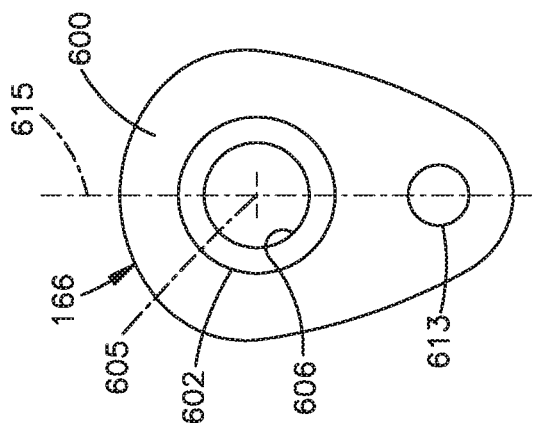
FIG. 26 depicts an alternative embodiment of an electrode connector.
Figure 25:
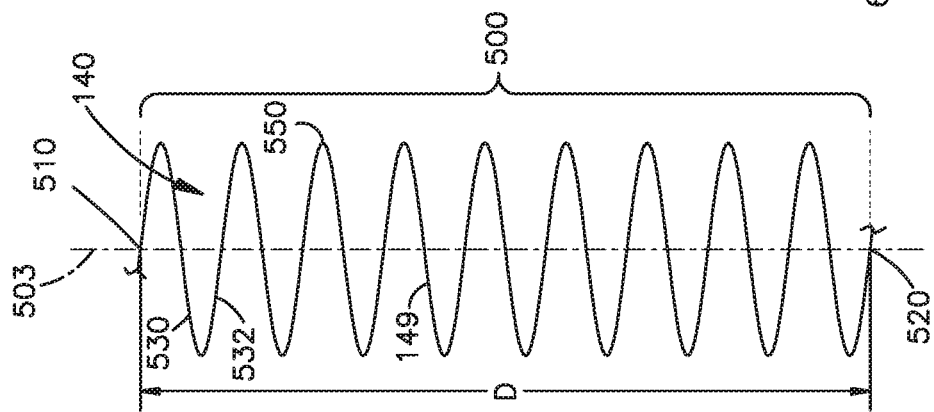
FIGS. 23-25 depict alternative embodiments of a conductor.

An alternative configuration of the electrode connector 166 is shown in FIG. 26. In this configuration, the base 600 of the connector 160 has an aperture 613 for a fastener to connect the conductor 140 to the base 600. The base 600 also has a generally oblong peripheral shape that is elongated on a longitudinal centerline 615. The elongated configuration of the base 600 provides space for the aperture 613 without the need to widen the base 600 laterally relative to the size of the circular base 600 in the embodiment of FIG. 22. The electrode connector 166 can thus fit more compactly beside and between adjacent connectors 166 that are aligned in the axial directions 503 shown in FIGS. 23, 24, and 25.

Figure 27:
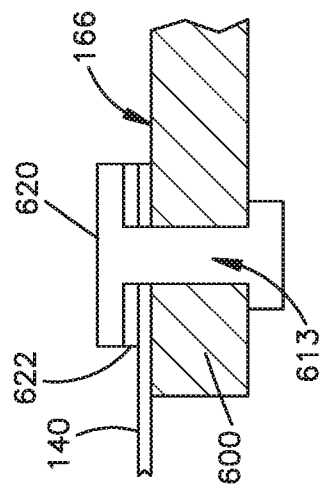
FIG. 27 depicts the connector of FIG. 26 in connection with other parts.

As shown in FIG. 27, the fastener can be a rivet 620, which is preferably formed of stainless steel. A compliant washer 622 is clamped between the rivet 620 and the conductive path 140 to prevent the conductive path 140 from being damaged by the rivet 620.

It should now be understood that the embodiments described herein can provide relatively durable and comfortable conductive human interfaces. The EMG signals can be communicated to signal processing devices that are located external to the conductive human interface by flexible and durable conductive paths. Moreover, the conductive interfaces can include sensors for providing additional control input. For example, temperature sensors, moisture sensors, or both can be used to control temperature control devices provided in the interface (e.g., prosthetic liner). Alternatively or additionally, the sensors can be configured to detect contact pressures, which can be used as control input to alter the shape or operation of an assistive device. Specifically, signals from the calf area can be used to control an ankle foot orthosis to adjust the stiffness of the device or the position of the components (e.g., ankle location). Moreover, feedback signals can be provided to the user via electrodes to help the user sense and control assistive devices.

There are other benefits that arise from inserting electrodes into a flexible liner, including increasing the number of muscle sites that can be accessed for collecting EMG signals. In a traditional EMG controlled prosthesis, the electrodes are inserted directly into a substantially rigid socket or inner socket. In this traditional configuration, EMG electrodes cannot be used to collect information from regions of the user's body that extend substantially outside of the socket. This limits the receptive field for EMG signals to tissues that are substantially inside of the socket. Use of a flexible liner with integrated electrodes allows electrodes to be applied to regions of tissue that extend beyond the socket. This allows for EMG signals to be collected from regions of tissue that extend across a joint. For example, in a traditional below elbow EMG controlled prosthesis, electrodes could only be placed in the socket and EMG signal collection would be limited to tissues at or below the elbow. However, muscles that control the wrist and hand are known to originate above the elbow and cross the elbow joint. By utilizing a flexible liner with embedded electrodes, the liner can extend beyond the socket, across the elbow, and allow EMG signals to be collected from above the elbow. For this reason, a flexible liner with embedded electrodes that extends beyond the socket allows for the collection of additional information that can be used to control a prosthetic wrist and hand from, for example, the supinator muscle, the pronator teres muscle, and other muscles, which would not be available with traditional EMG control. This additional information can improve the user's control over pronation and supination and other functions. This benefit is not limited to pronation and supination, below elbow applications, or upper extremity prosthetics. As examples, expansion of the EMG receptive field across the elbow can also benefit other functions such as wrist flexion/extension and finger flexion/extension in the upper extremity prosthesis, while placement of electrodes above the knee could collect information from the plantaris muscle to facilitate control of ankle flexion of prostheses for below knee amputees.

Figure 28:
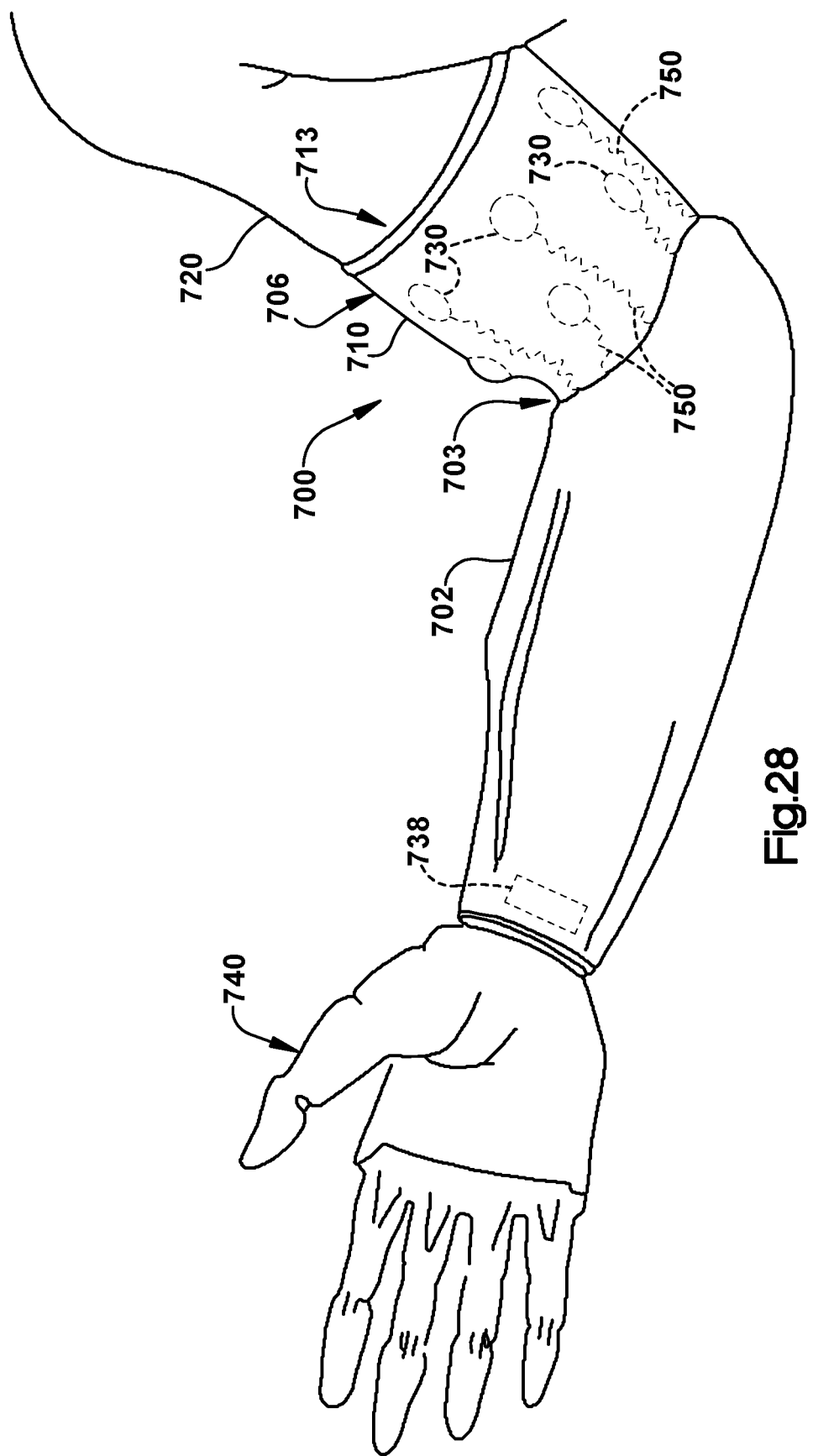
FIG. 28 depicts an alternative embodiment of a conductive human interface.

As an example of the foregoing considerations, the conductive human interface 700 of FIG. 28 is associated with a socket 702. The socket 702 has a socket opening 703 for insertion of a liner 706. The liner 706 has a proximal end portion 710 with a liner opening 713 for insertion of a residual limb 720. The liner 706 takes an operative position in which a distal end portion of the liner 706 is received in the socket 702, and the proximal end portion 710 projects outward from the socket opening 703. An array of electrodes or sensors 730 are mounted on the proximal end portion 710 of the liner 706 in the same or substantially the same manner as described above regarding the electrodes 130, and are configured to electrically connect with the residual limb 720.

As shown schematically in FIG. 28, an electrical connector 738 is included to electrically connect the electrodes or sensors 730 with a prosthetic device 740. A corresponding array of conductive paths 750 interconnect the electrodes or sensors with the electrical connector 738. The conductive paths 750 can be configured in the same or substantially the same manner as the conductive paths 140 described above. One or more of the conductive paths 750 may reach through the socket opening 703 from the proximal end portion 710 of the liner 706 to the distal end portion when the when the liner 706 is in the operative position.

This written description sets for the best mode of carrying out the invention, and describes the invention so as to enable a person of ordinary skill in the art to make and use the invention, by presenting examples of the elements recited in the claims. The detailed descriptions of those elements do not impose limitations that are not recited in the claims, either literally or under the doctrine of equivalents.

What is claimed is:

1. A conductive human interface, consisting of:
a fabric layer flexible substrate having an interior surface and an exterior surface;
a coating of a soft polymer applied in a gel state that covers the interior surface of the fabric layer, such that the interior surface forms a boundary with the soft coating;
an electrode or sensor configured to electrically connect with a residual limb, the electrode or sensor protruding away from the interior surface of the fabric layer through the soft coating;
a cord of conductive thread embedded within the soft coating that extends through and is spaced from the interior surface of the fabric layer, the cord of conductive thread connecting the electrode with an electrical connector; and
nonconductive support thread extending through the fabric layer from the exterior surface thereof to the interior surface to extend around the cord of conductive thread, the nonconductive support thread being dissoluble for removal from the interface by dissolving in a solvent, such that upon removal of the nonconductive support thread a space is created allowing for shifting of the cord of conductive thread in response to forces imparted from the residual limb.

2. The interface of claim 1, wherein the cord of conductive thread is formed of filaments that are bundled, spun, or twisted together.

3. The interface of claim 2 wherein the filaments include filaments that are formed of electrically nonconductive material and are coated or embedded with electrically conductive elements.

4. The interface of claim 2, wherein the filaments include filaments that are formed of electrically conductive material.

5. The interface of claim 4, wherein the electrically conductive material includes stainless steel.

6. The interface of claim 1, wherein the cord of conductive thread has a monofilament structure.

7. The interface of claim 6, wherein the monofilament structure is a filament formed of stainless steel.

8. The interface of claim 1, wherein the fabric layer is stretchable in a stretchable direction, and wherein the cord of conductive thread has an extendable length portion with a first end, a second end spaced from the first end at a linear distance in the stretchable direction, and a length greater than the linear distance, whereby the greater length enables the cord of conductive thread to elongate in the stretchable direction when the fabric layer stretches in the stretchable direction.

9. The interface of claim 8, wherein the stretchable direction is a longitudinal direction in which the first end of the extendable length portion is a proximal end and the second end is a distal end.

10. The interface of claim 8, wherein the extendable length portion of the cord of conductive thread has first segments reaching toward the second end in orientations toward one side of the stretchable direction and has second segments reaching toward the second end in orientations toward an opposite side of the stretchable direction.

11. The interface of claim 10, wherein the first and second segments include segments that are linear and reach toward the second end in a zig-zag configuration with corners between adjacent segments.

12. The interface of claim 10, wherein the first and second segments include segments that are arcuate and reach toward the second end in a serpentine configuration with turns between adjacent segments.

13. The interface of claim 1, wherein the support thread is dissoluble in water.

14. The interface of claim 1, wherein the cord of conductive thread is subdivided into an electrical conductor and an electrical connector configured to connect with a prosthetic or other assistive device, a sensor at least partially embedded in the soft coating and the electrical conductor is part of a conductive path electrically interconnecting the sensor with the electrical connector.

15. The interface of claim 1, wherein the cord of conductive thread is stitched with an aspect ratio greater than 1.

16. The interface of claim 1, wherein the cord of conductive thread comprises multiple plies.

17. The interface of claim 1, wherein the cord of conductive thread has a linear resistance of less than about 10 Ω/in.

18. The interface of claim 1, wherein the cord of conductive thread has a linear density of at least 2,000 yd/lb.

19. The conductive human interface of claim 1, wherein the cord of conductive thread is flexible.

\* \* \* \* \*